United States Patent
Ghosh et al.

(10) Patent No.: US 11,230,550 B2
(45) Date of Patent: Jan. 25, 2022

(54) MACROCYCLIC HIV-1 PROTEASE INHIBITORS AND USES THEREOF

(71) Applicant: Purdue Research Foundation, West Lafayette, IN (US)

(72) Inventors: Arun K. Ghosh, West Lafayette, IN (US); Hiroaki Mitsuya, Kumamoto (JP); Sean Fyvie, West Lafayette, IN (US); Margherita Brindisi, Corleto Perticara (IT)

(73) Assignee: Purdue Research Foundation, West Lafayette, IN (US)

( * ) Notice: Subject to any disclaimer, the term of this patent is extended or adjusted under 35 U.S.C. 154(b) by 4 days.

(21) Appl. No.: 16/627,697

(22) PCT Filed: Jun. 29, 2018

(86) PCT No.: PCT/US2018/040342
§ 371 (c)(1),
(2) Date: Dec. 30, 2019

(87) PCT Pub. No.: WO2019/006335
PCT Pub. Date: Jan. 3, 2019

(65) Prior Publication Data
US 2020/0165264 A1  May 28, 2020

Related U.S. Application Data

(60) Provisional application No. 62/527,768, filed on Jun. 30, 2017.

(51) Int. Cl.
*C07D 493/04* (2006.01)
*C07D 519/00* (2006.01)

(52) U.S. Cl.
CPC ......... *C07D 493/04* (2013.01); *C07D 519/00* (2013.01)

(58) Field of Classification Search
CPC .................. C07D 493/04; C07D 519/00
See application file for complete search history.

(56) References Cited

U.S. PATENT DOCUMENTS

2015/0111962 A1  4/2015  Ghosh
2017/0088555 A1  3/2017  Ghosh et al.

FOREIGN PATENT DOCUMENTS

WO  WO-2017031220 A1  2/2017
WO  WO-2019006335 A1  1/2019

OTHER PUBLICATIONS

Merriam-Webster, Definition of isomer, obtained from https://www.merriam-webster.com/dictionary/isomer on Feb. 27, 2021 (Year: 2021).*
Dörwald, F. Zaragoza. Side Reactions in Organic Synthesis: A Guide to Successful Synthesis Design, Weinheim: WILEY-VCH Verlag GmbH & Co. KGaA, 2005, Preface (Year: 2005).*
Ghosh et al. Bioorg. Med. Chem. Lett. 2017, 27, 4925-4931 (Year: 2017).*
"International Application Serial No. PCT/US2018/040342, International Preliminary Report on Patentability dated Jan. 9, 2020", 7 pgs.
"International Application Serial No. PCT/US2018/040342, International Search Report dated Nov. 15, 2018", 4 pgs.
"International Application Serial No. PCT/US2018/040342, Invitation to Pay Add'l Fees and Partial Search Report dated Sep. 7, 2018", 2 pgs.
"International Application Serial No. PCT/US2018/040342, Written Opinion dated Nov. 15, 2018", 5 pgs.
Ghosh, et al., "Design, Synthesis, Protein-Ligand X-ray Structure, and Biological Evaluation of a Series of Novel Macrocyclic Human Immunodeficiency Virus-1 Protease Inhibitors to Combat Drug Resistance", J. Med. Chem, (2009), 7689-7705.

* cited by examiner

*Primary Examiner* — Matthew P Coughlin
(74) *Attorney, Agent, or Firm* — Schwegman Lundberg & Woessner, P.A.

(57) ABSTRACT

Described herein are compounds of the formulae (I), (Ia), (Ib), and (II) and pharmaceutically acceptable salts, isomers, mixture of isomers, crystalline forms, non-crystalline forms, hydrates, or solvates thereof, as well as methods of making and using compounds of the formulae (I), (Ia), (Ib), and (II) to, among other things, treat HIV/AIDS.

20 Claims, No Drawings

MACROCYCLIC HIV-1 PROTEASE INHIBITORS AND USES THEREOF

RELATED APPLICATIONS

This application is a U.S. national stage application under 37 C.F.R. 371(b) of International Application Serial No. PCT/US2018/040342, filed 29 Jun. 2018, which claims priority under 35 § 119(e) to U.S. Provisional Application Ser. No. 62/527,768, filed 30 Jun. 2017.

STATEMENT OF U.S. GOVERNMENT SUPPORT

This invention was made with government support under GM053386 awarded by the National Institutes of Health. The government has certain rights in the invention.

BACKGROUND OF THE INVENTION

HIV protease inhibitor-based active antiretroviral therapy (ART) has been proven to be most effective treatment regimens for HIV/AIDS. However, drug-side effects and emergence of drug-resistance are making ART far less effective or ineffective outright.

SUMMARY

The inventors have designed and developed a series of macrocyclic HIV-1 protease inhibitors based upon X-ray structure of an inhibitor-bound HIV-1 protease. The macrocyclic inhibitors of the various embodiments described herein are capable of forming extensive hydrogen bonding interactions with the HIV-1 protease enzyme active-site backbone, an important concept behind the development of compounds against resisted HIV. While not wishing to be bound by any specific theory, it is believed that inhibitors that contain a flexible macrocycle involving allow effective repacking at the mutation site. It is believed that this factor may influence the enzyme-inhibitory potency and antiviral potency of the compound of the various embodiments described herein. In addition, a number of the compounds of the various embodiments described herein have been shown to maintain potency against multi-drug-resistant HIV variants. This class of inhibitors may exhibit improved pharmacological properties compared to darunavir and other FDA approved-inhibitors.

DETAILED DESCRIPTION OF THE INVENTION

Reference will now be made in detail to certain examples of the disclosed subject matter. While the disclosed subject matter will be described in conjunction with the enumerated claims, it will be understood that the exemplified subject matter is not intended to limit the claims to the disclosed subject matter.

Various examples described herein are directed to a compound of the formula (I):

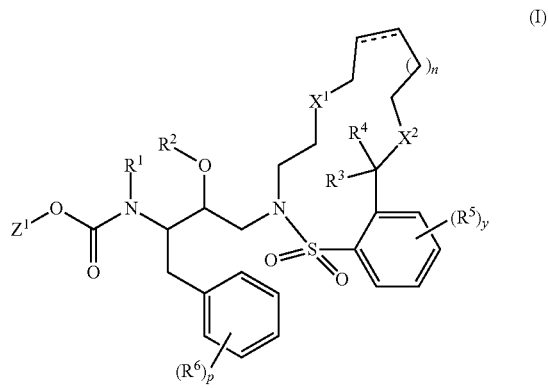

(I)

or a pharmaceutically acceptable salt, isomer, mixture of isomers, crystalline form, non crystalline form, hydrate, or solvate thereof wherein:
the dashed line represents an E- or Z-double bond;
Z is:

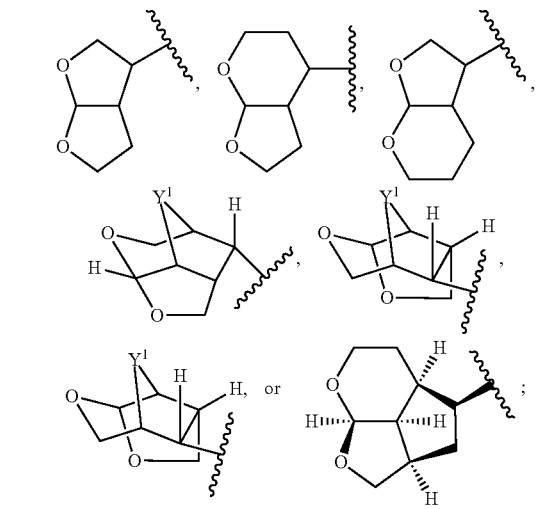

$R^1$ and $R^2$ are each independently hydrogen, alkyl or arylalkyl;
$R^3$ and $R^4$ are each independently H, alkyl or $R^3$ and $R^4$, together with the carbon atom to which they are attached, form a cycloalkyl or a heterocyclyl group;
$Y^1$ is optionally substituted alkylene (e.g., $CH_2$), O, or N—$R^a$, wherein $R^a$ is hydrogen or alkyl;
$X^1$ and $X^2$ are each independently oxygen, S, S(O), $SO_2$, optionally substituted nitrogen, or optionally substituted alkylene;
each $R^5$ is independently hydrogen, —$OR^b$, wherein $R^b$ is alkyl or aryl, —$SO_2R^7$, —$NR_2^7$, —$CHR^7OR^7$ or $CR_3^7$, wherein each $R^7$ is independently hydrogen, alkyl, heteroalkyl or heterocyclyl or two adjacent $R^5$ groups, together with the carbon atoms to which they are attached, form a heteroaryl group;
each $R^6$ is independently hydrogen, halo (e.g., mono-fluoro and di-fluoro), —$NR_2^7$, alkyl, aryl, alkylaryl, heteroalkyl or heterocyclyl;

y is an integer from 1 to 3; (e.g., 1);

p is an integer from 1 to 3 (e.g., 1 or 2); and n is an integer from 0-4 (e.g., an integer from 1-4).

Various examples described herein are directed to a compound of the formula (Ia):

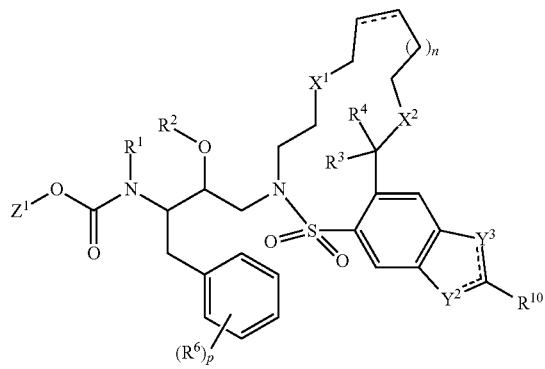

(Ia)

or a pharmaceutically acceptable salt, isomer, mixture of isomers, crystalline form, non crystalline form, hydrate, or solvate thereof wherein:

the dashed line represents an E- or Z-double bond;

$Z^1$ is:

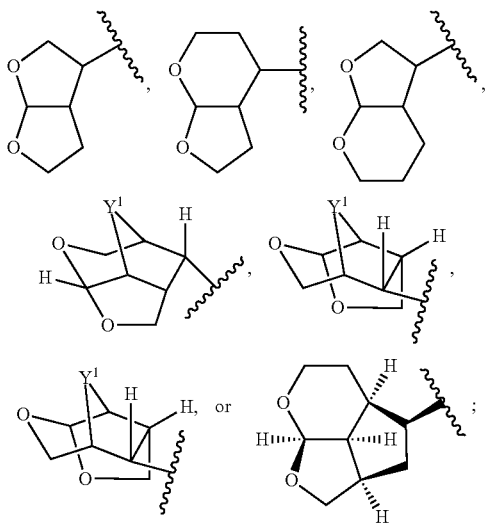

$R^1$ and $R^2$ are each independently hydrogen, alkyl or aryl-alkyl;

$R^3$ and $R^4$ are each independently H, alkyl or $R^3$ and $R^4$, together with the carbon atom to which they are attached, form a cycloalkyl or a heterocyclyl group;

$Y^1$ is optionally substituted alkylene (e.g., $CH_2$), O, or N—$R^a$, wherein $R^a$ is hydrogen or alkyl;

$X^1$ and $X^2$ are each independently oxygen, S, S(O), $SO_2$, optionally substituted nitrogen, or optionally substituted alkylene;

each $R^6$ is independently hydrogen, halo (e.g., mono-fluoro and di-fluoro), —$NR_2^7$, alkyl, aryl, alkylaryl, heteroalkyl or heterocyclyl;

$R^{10}$ is —$OR^9$ or —$NR_2^9$, wherein each $R^9$ is independently hydrogen, alkyl, cycloalkyl, heteroalkyl or heterocyclyl;

$Y^2$ and $Y^3$ are each independently NH, S, O, $NR^9$ or $CR_2^{11}$, wherein each $R^{11}$ is independently hydrogen, alkyl, aryl, or heterocyclyl;

p is an integer from 1 to 3 (e.g., 1 or 2); and n is an integer from 0-4 (e.g., an integer from 1-4).

In some embodiments, the compounds of the formula (I) and (Ia) are compounds of the formula:

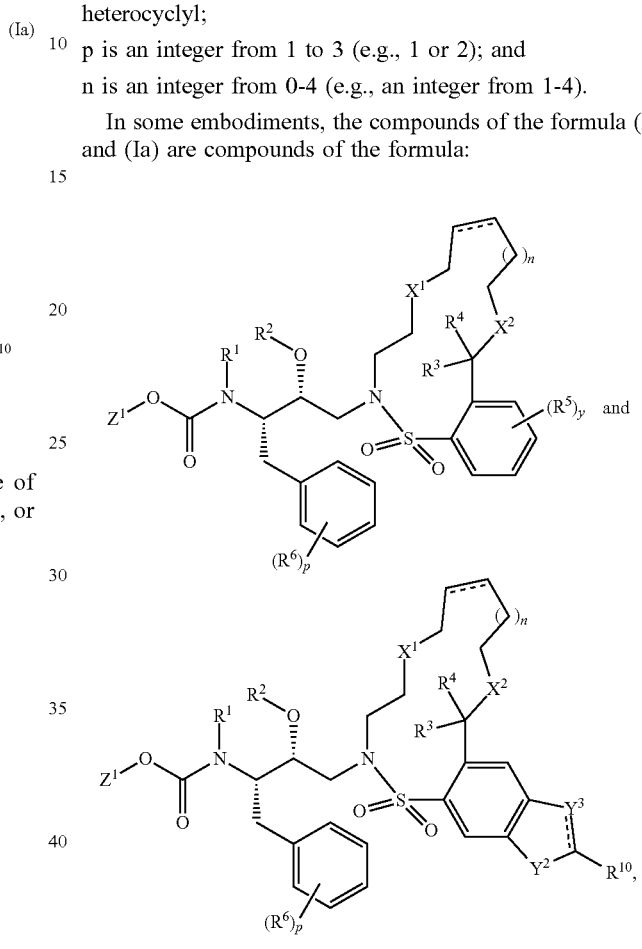

respectively.

Various other examples described herein are directed to compounds of the formula (Ib):

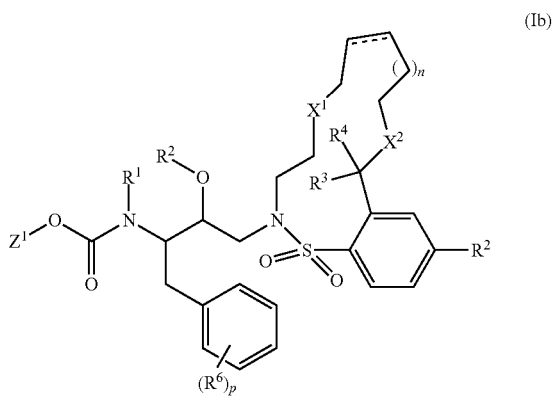

(Ib)

or a pharmaceutically acceptable salt, isomer, mixture of isomers, crystalline form, non crystalline form, hydrate, or solvate thereof wherein:

the dashed line represents an E- or Z-double bond;

$Z^1$ is:

[chemical structures]

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, S, S(O), $SO_2$, optionally substituted nitrogen, or optionally substituted alkylene;

$R^5$ is hydrogen, $-OR^b$, wherein $R^b$ is alkyl or aryl, $-SO_2R^7$, $-NR_2^7$, $-CHR^7OR^7$ or $CR_3^7$, wherein each $R^7$ is independently hydrogen, alkyl, heteroalkyl or heterocyclyl or two adjacent $R^5$ groups, together with the carbon atoms to which they are attached, form a heteroaryl group;

each $R^6$ is independently hydrogen, halo (e.g., mono-fluoro and di-fluoro), $-NR_2^7$, alkyl, aryl, alkylaryl, heteroalkyl or heterocyclyl;

p is an integer from 1 to 3 (e.g., 1 or 2); and n is an integer from 0-4 (e.g., an integer from 1-4).

In some embodiments of the compounds of the formula (Ib), the group $Z^1$ is a group of the formula:

[chemical structures]

Various examples described herein are directed to a compound of the formula (II):

(II)

[chemical structure]

or a pharmaceutically acceptable salt, isomer, mixture of isomers, crystalline form, non crystalline form, hydrate, or solvate thereof wherein:

the dashed line represents an E- or Z-double bond;

$Z^2$ is:

[chemical structures]

wherein $R^8$ is $-OR^9$ or $-NR_2^9$, wherein each $R^9$ is independently hydrogen, alkyl, heteroalkyl or heterocyclyl;

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, S, S(O), $SO_2$, optionally substituted nitrogen, or optionally substituted alkylene;

each $R^5$ is independently hydrogen, $-OR^b$, wherein $R^b$ is alkyl or aryl, $-SO_2R^7$, $-NR_2^7$, $-CHR^7OR^7$ or $CR_3^7$, wherein each $R^7$ is independently hydrogen, alkyl, heteroalkyl or heterocyclyl or two adjacent $R^5$ groups, together with the carbon atoms to which they are attached, form a heteroaryl group;

each $R^6$ is independently hydrogen, halo, $-NR_2^7$, alkyl, aryl, alkylaryl, heteroalkyl or heterocyclyl;

y is an integer from 1 to 3; (e.g., 1);

p is an integer from 1 to 3 (e.g., 1 or 2); and n is an integer from 0-4 (e.g., an integer from 1-4).

In some embodiments of the compounds of the formula (II), the group $Z^2$ is a group of the formula:

[chemical structures]

wherein $R^8$ is $-OR^9$ or $-NR_2^9$, wherein each $R^9$ is independently hydrogen, alkyl, heteroalkyl or heterocyclyl.

Examples of compounds encompassed by the formulae (I), (Ia), (Ib), and (II) include:
1
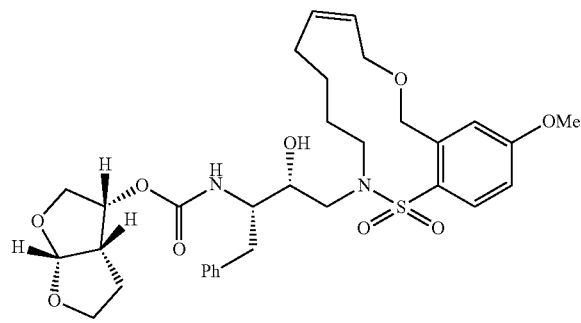
2
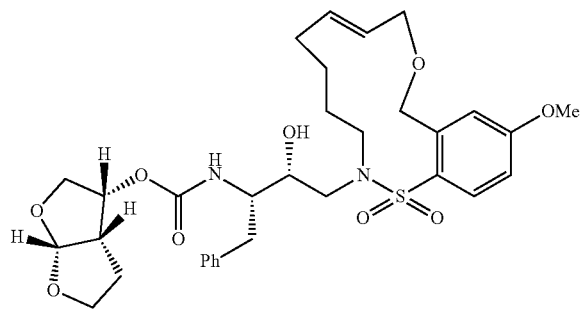
3
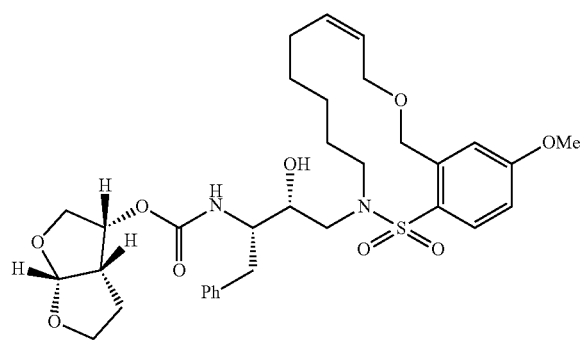
4
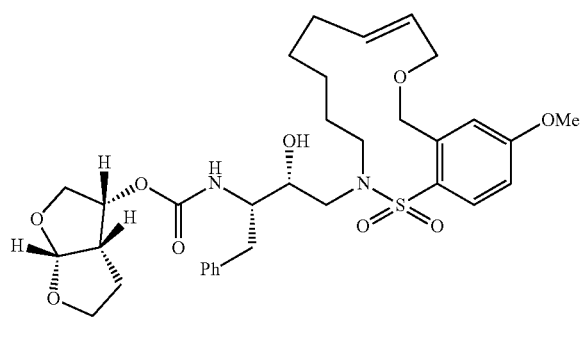
5
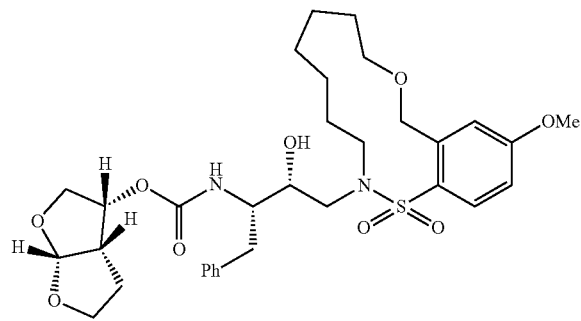
6
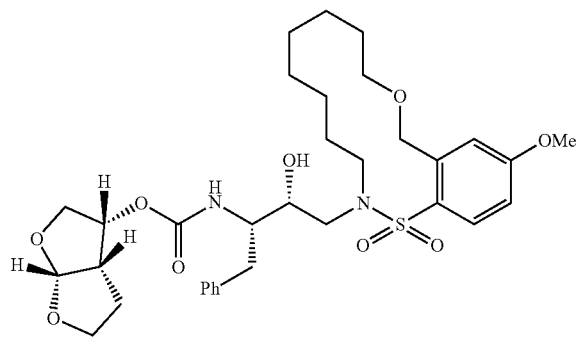
7
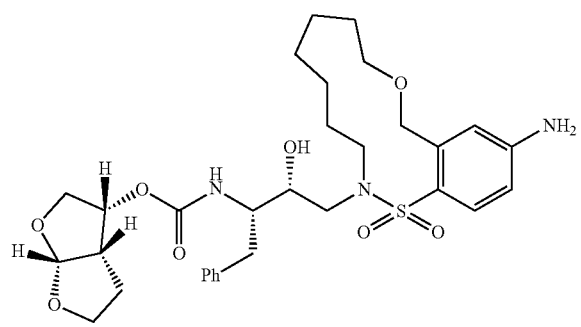
8
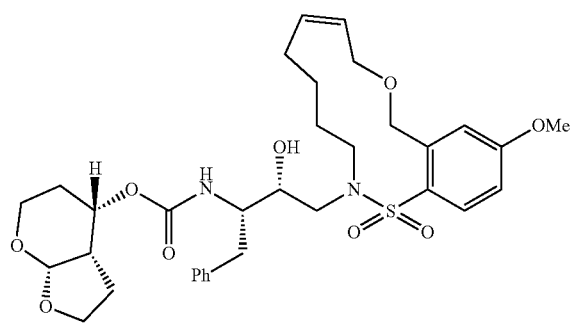

9
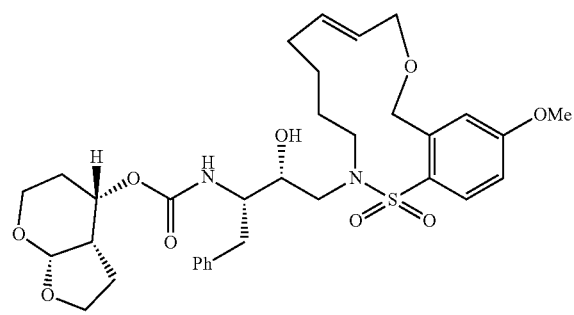
10
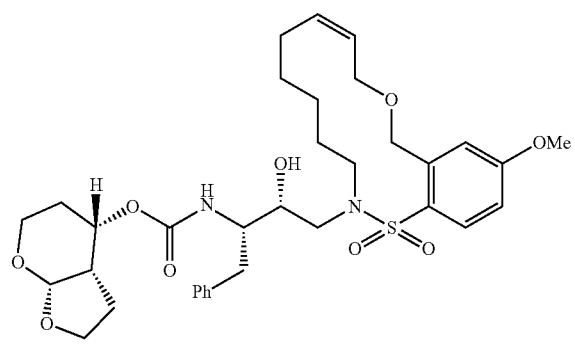
11
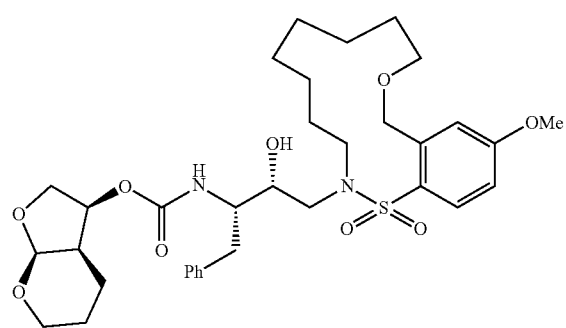
12
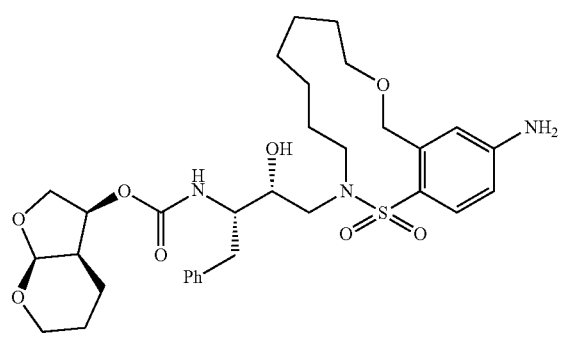
13
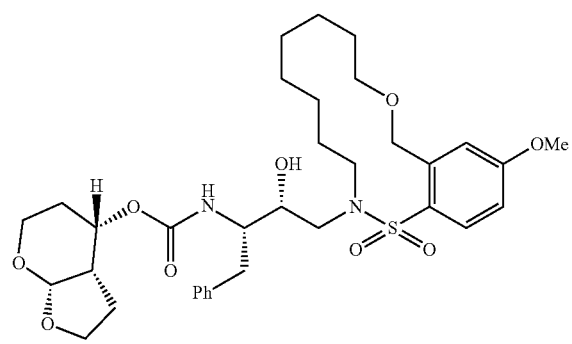
14
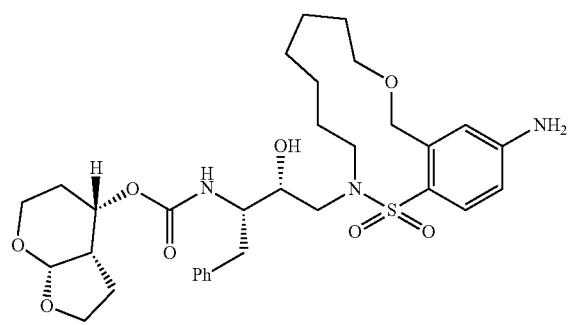
15
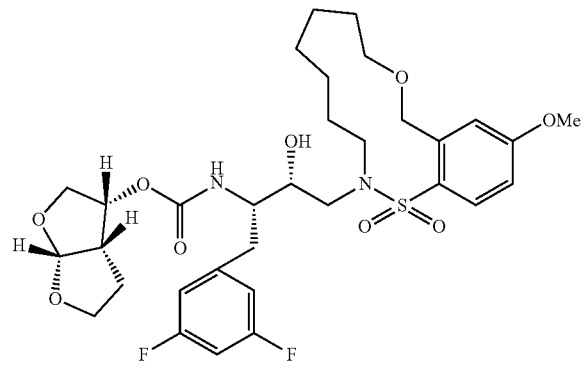
16
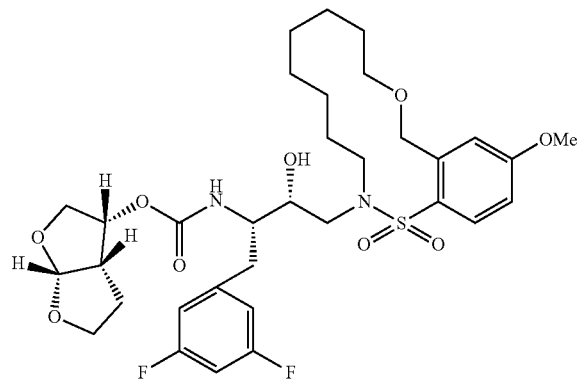

17
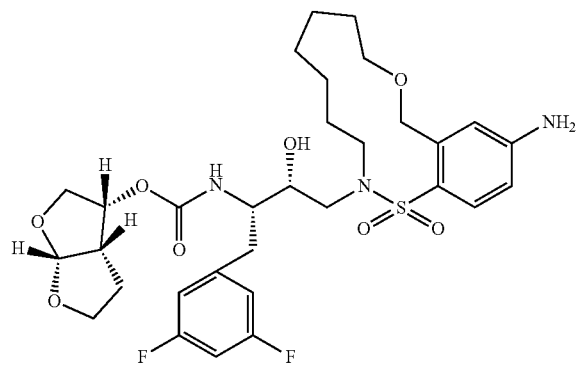
18
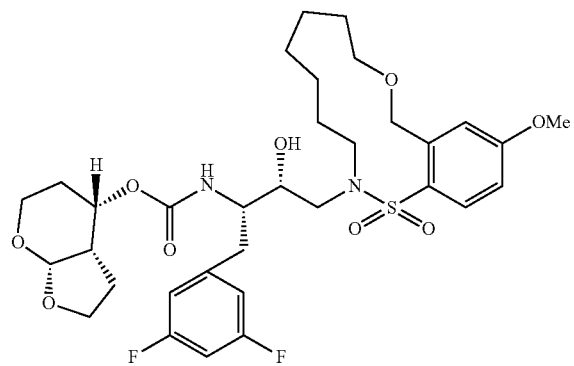
19
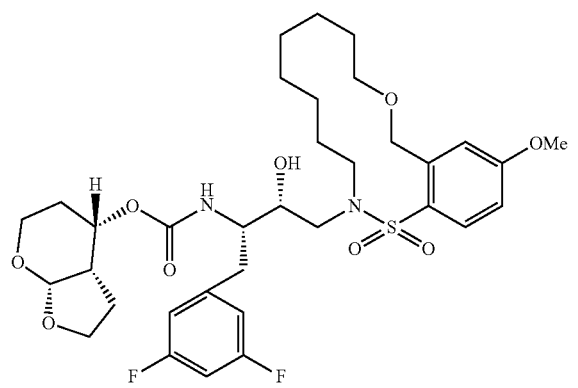
20
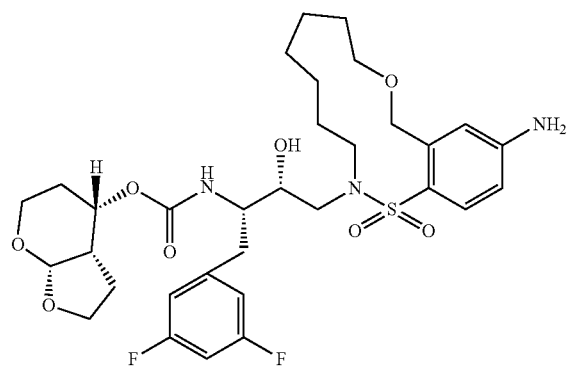
21
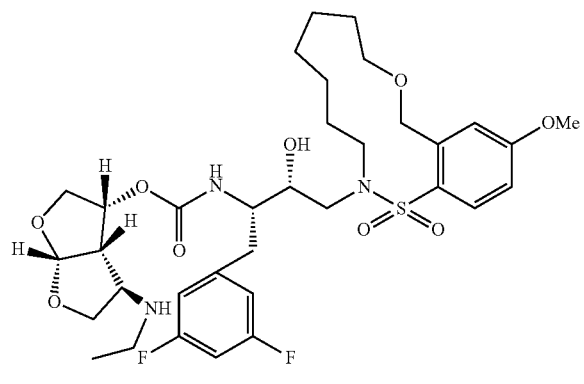
22
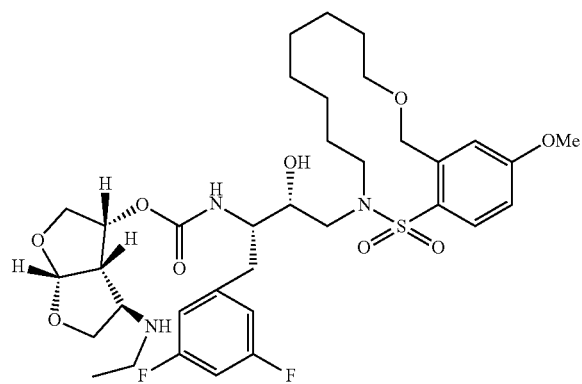
23
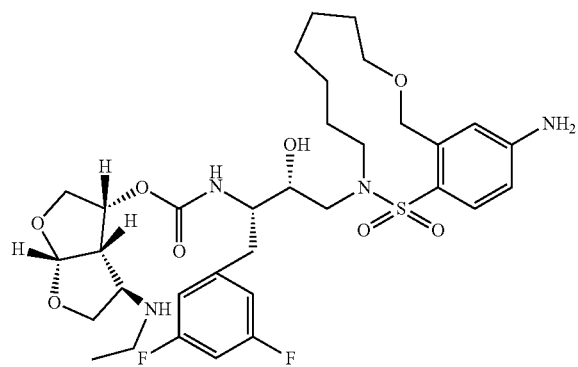
24
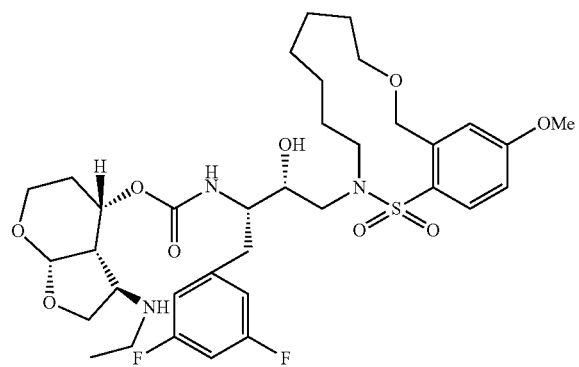

-continued
| 25 | 26 |
|---|---|
| 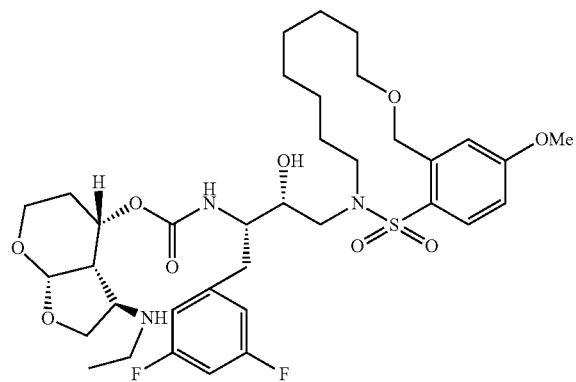 | 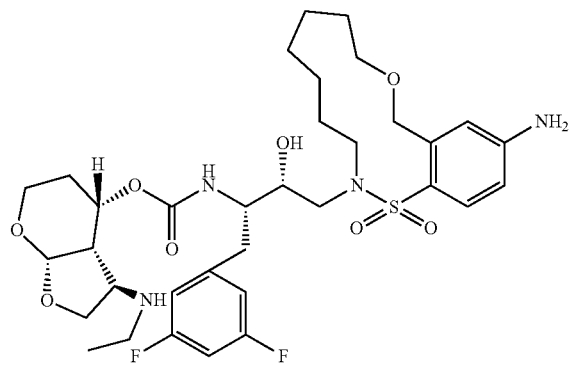 |
| 27 | 28 |
| 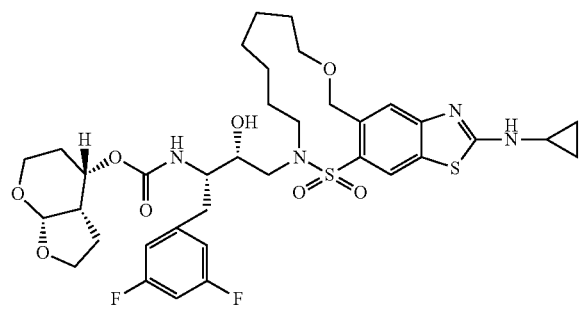 | 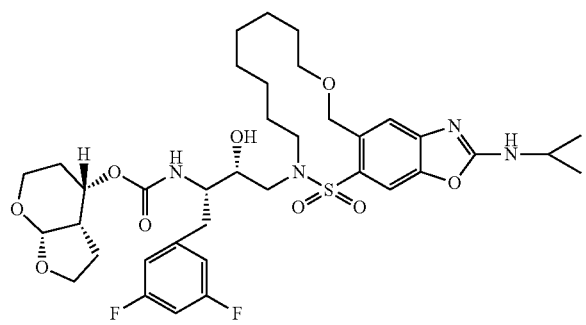 |
| 29 | 30 |
| 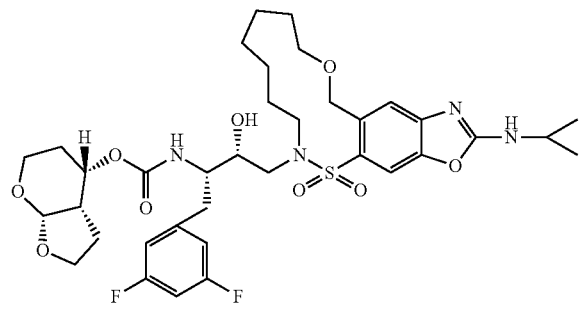 | 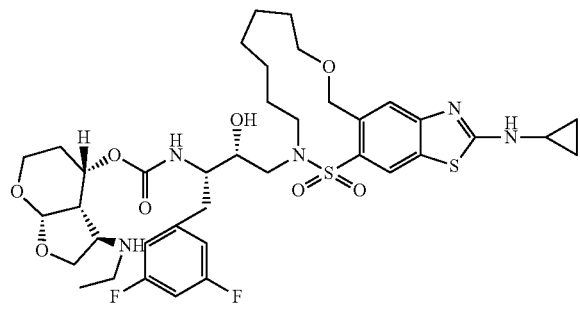 |
| 31 | 32 |
| 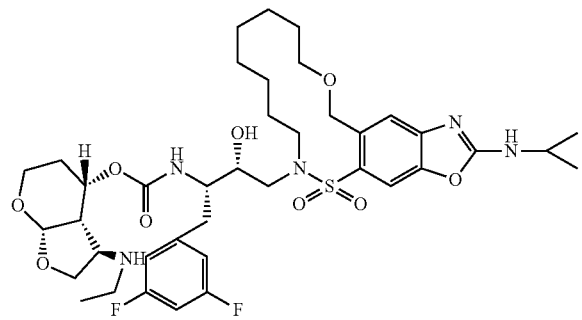 | 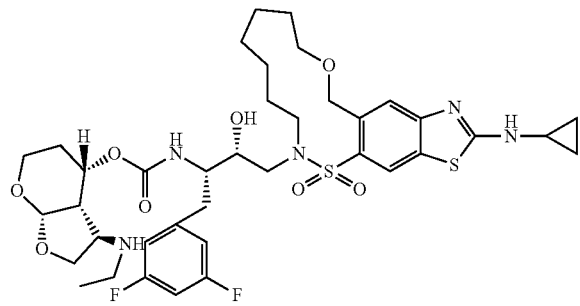 |

-continued
33
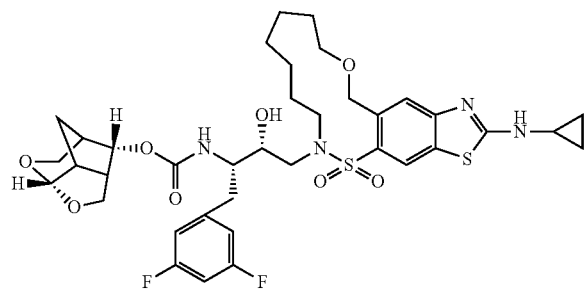
34
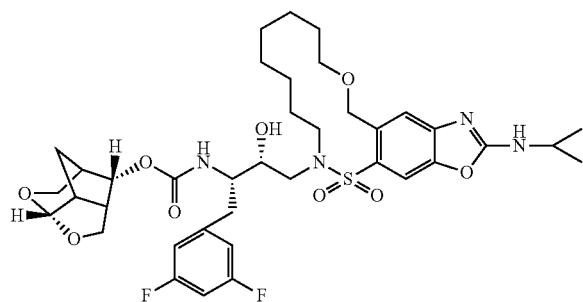
35
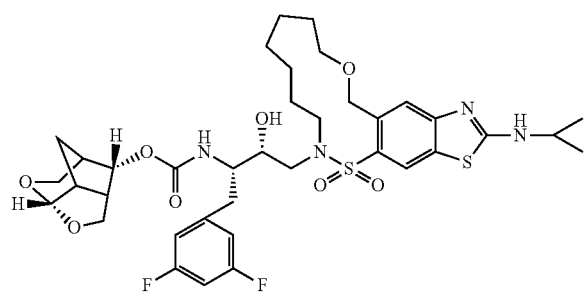
36
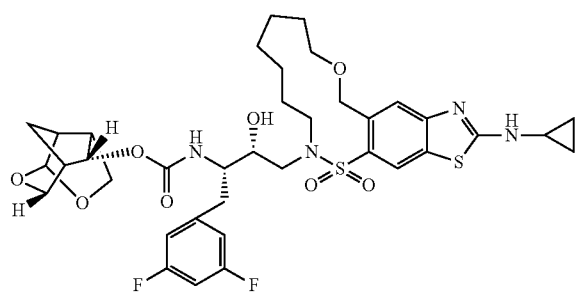
37
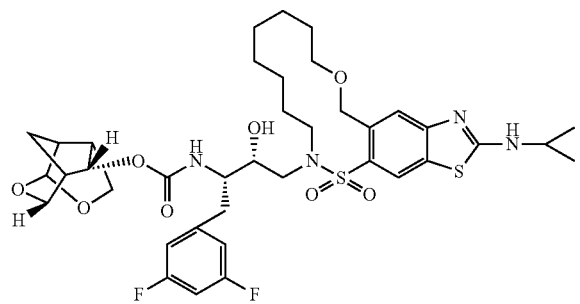
38
54
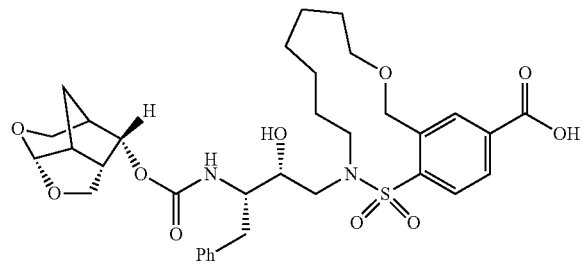
55
56
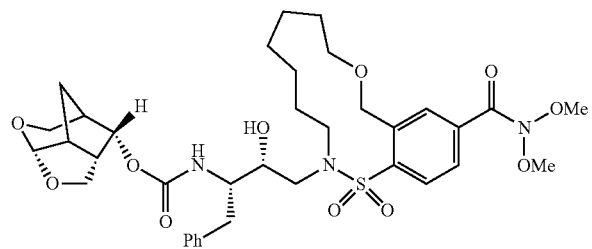
57
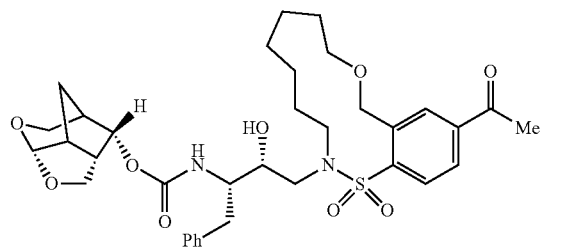

-continued
58
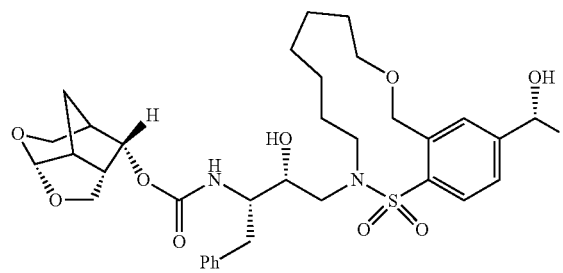
59
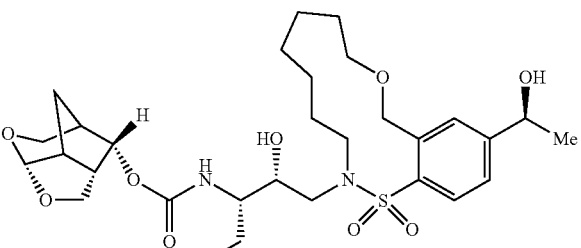
60
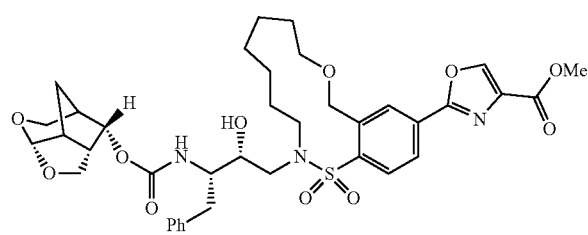
61
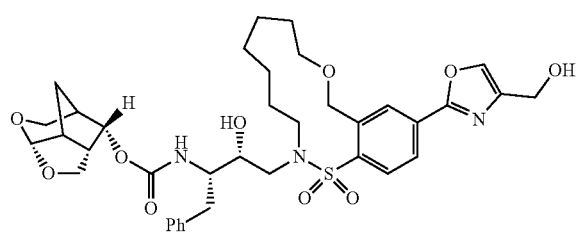
62
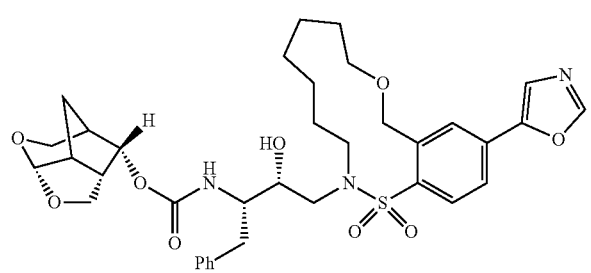
63
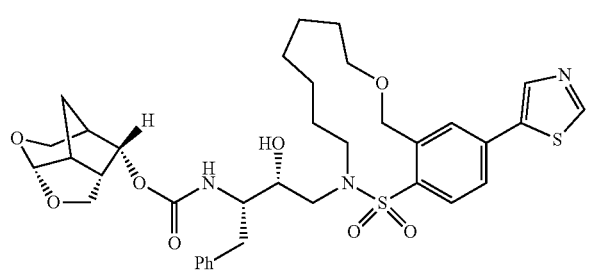
64
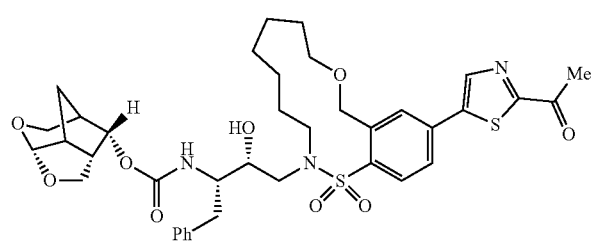
65
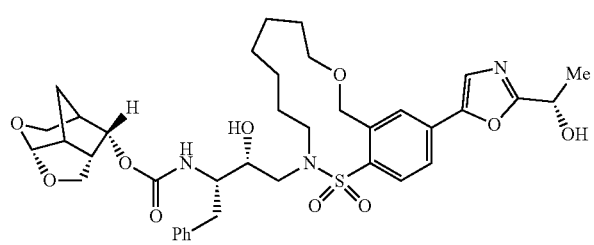
66
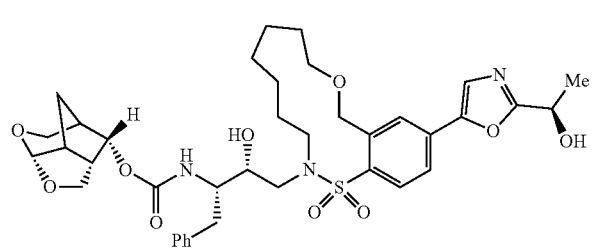
67
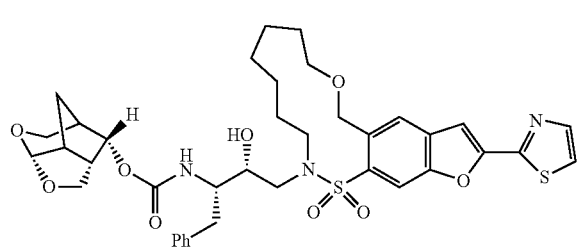
68
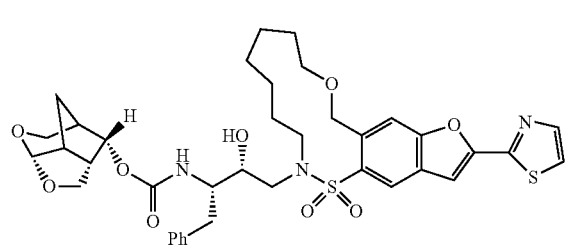

-continued
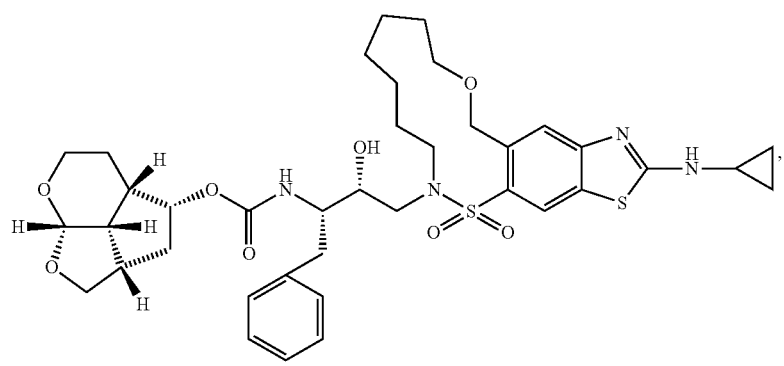
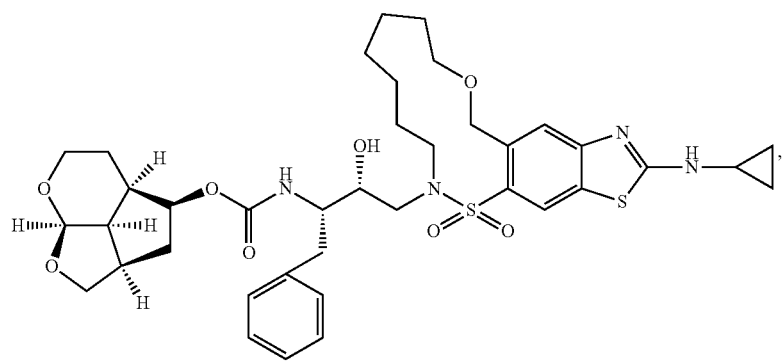
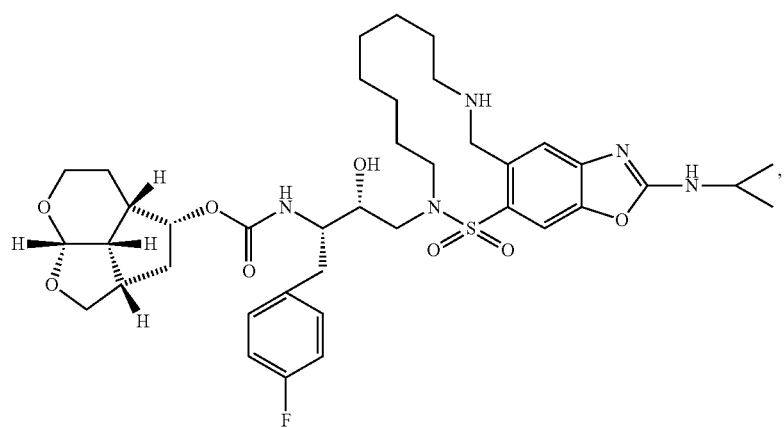
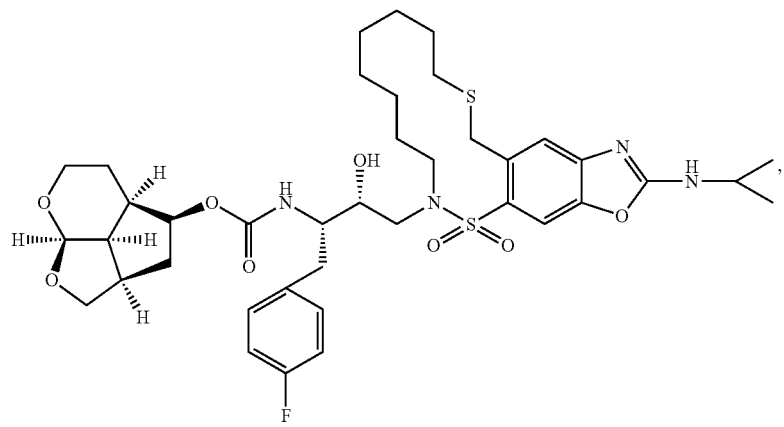

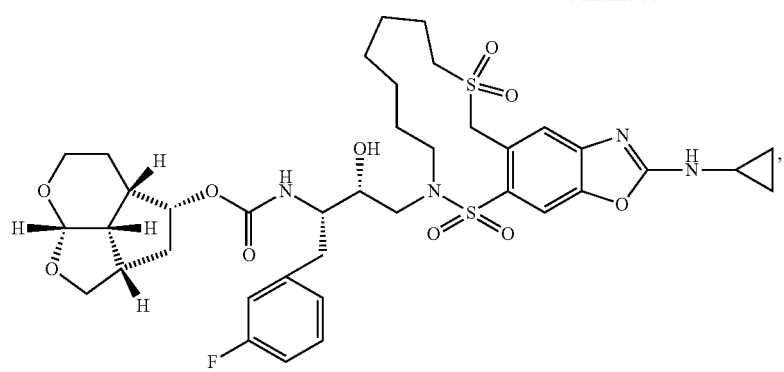
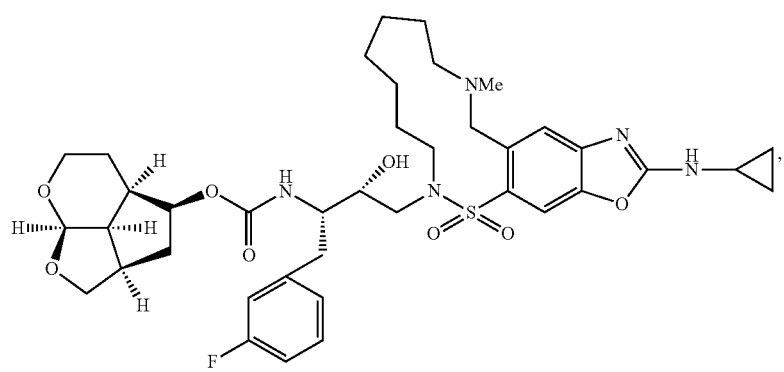
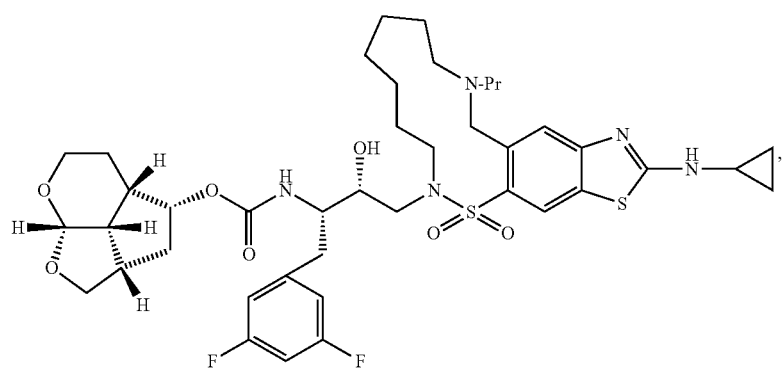
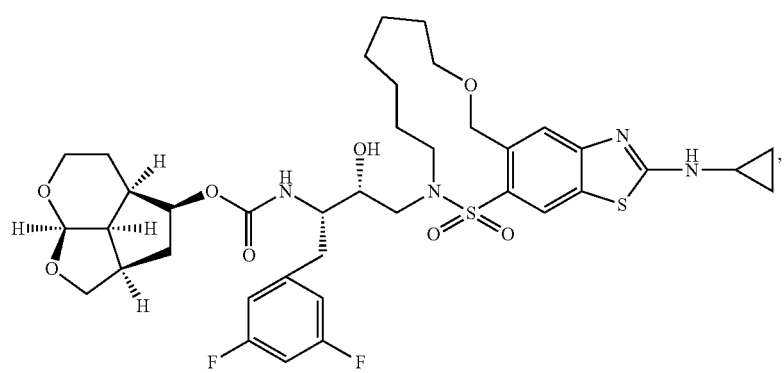

-continued

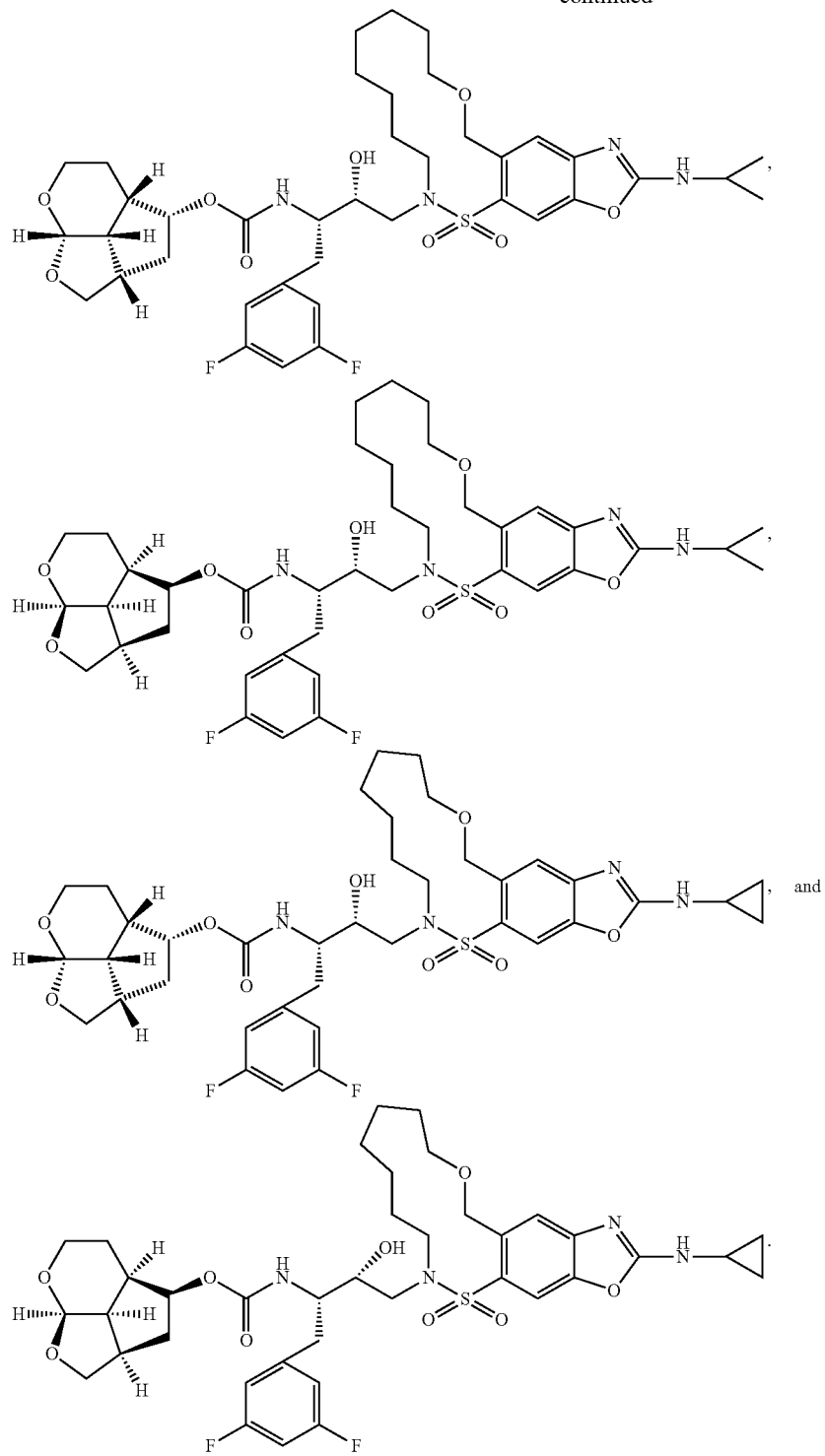

Those of ordinary skill in the art will recognize that compounds described herein can contain chiral centers. All diastereomers of the compounds described herein are contemplated herein, as well as racemates.

Various examples of the present invention also contemplate pharmaceutical compositions comprising one or more compounds of the various examples of the present invention (e.g., compounds of the formulae (I), (Ia), (Ib), and (II)) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one example, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited examples, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurysulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various examples of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited examples, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one example, the dosage may be administered daily for up to and including 30 days, preferably between 7-10 days. In another example, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some examples, the various examples of the present invention contemplate pharmaceutical compositions comprising a therapeutically effective amount of one or more compounds of the various examples of the present invention. In some aspects, the various examples of the present invention contemplate a compound of the formulae (I), (Ia), (Ib), and (II) for use as a medicament for treating a patient in need of relief from a disease or a condition, such as HIV/AIDS. Other embodiments are directed to a method for treating a patient (e.g., a human patient) in need of relief from HIV/AIDS, the method comprising the step of administering to the patient a therapeutically effective amount of a compound of the formula (I), (Ia), (Ib) or (II) or a pharmaceutical composition comprising a therapeutically effective amount of a compound of the formula (I), (Ia), (Ib) or (II).

The term "therapeutically effective amount" as used herein, refers to that amount of one or more compounds of the various examples of the present invention that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some examples, the compounds of the various examples of the present invention have a half maximal inhibitory concentration ($IC_{50}$) of from about 5 nM to about 500 nM (e.g., about 50 nM to about 100 nM, about 10 nM to about 75 nM, about 10 nM to about 60 nM, about 100 nM to about 500 nM, about 50 µM to about 250 nM, about 100 nM to about 300 nM or about 10 nM to about 30 nM).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z" unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" and "optionally substituted" as used herein refers to a group (e.g., alkyl, aryl, and heteroaryl) or molecule in which one or more hydrogen atoms contained thereon are replaced by one or more substituents. The term "substituent" as used herein refers to a group that can be or is substituted onto a molecule or onto a group. Examples of substituents include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be, for example, hydrogen, alkyl, acyl, cycloalkyl, aryl, aralkyl, heterocyclyl, heteroaryl, or heteroarylalkyl.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some examples, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, so-butyl, sec-butyl, t-butyl, neopentyl, isopentyl, and 2,2-dimethylpropyl groups. Representative substituted alkyl groups can be substituted one or more times with any of the groups listed herein, for example, amino, hydroxy, cyano, carboxy, nitro, thio, alkoxy, and halogen groups.

As used herein, the term "heteroalkyl" includes a chain of atoms that includes both carbon and at least one heteroatom such as, but not limited to, N, O, and S, and is optionally branched. In certain variations, illustrative heteroatoms also include phosphorus, and selenium.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some examples, the cycloalkyl group can have 3 to about 8-12 ring members, whereas in other examples the number of ring carbon atoms range from 3 to 4, 5, 6, or 7. In some examples, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some examples, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some examples, heterocyclyl groups include 3 to about 20 ring members, whereas other such groups have 3 to about 15 ring members. In some examples, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$), 3 to 4 carbon atoms ($C_3$-$C_4$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an example of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to alkylamines, arylamines, arylalkylamines; dialkylamines, diarylamines, diaralkylamines, heterocyclylamines and the like; and ammonium ions.

The terms "halo," "halogen," or "halide" group, as used herein, by themselves or as part of another substituent, mean, unless otherwise stated, a fluorine, chlorine, bromine, or iodine atom.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The present invention can be better understood by reference to the following examples which are offered by way of illustration. The present invention is not limited to the examples given herein.

Preparation of sulfonyl chloride 40 was carried out from commercially available 3-allyloxymethylanisole 39 by treatment with chlorosulfuric acid at 0° C. followed by reaction of the resulting sulfonic acid with cyanuric chloride in dry acetone in the presence of triethylamine to provide sulfonyl chloride 40 in 37% yield (Scheme 1). For the synthesis of benzyl ether derivative with 4-amino substitution, the corresponding sulfonyl chloride derivative 42 was prepared from commercially available 2-chloro-5-nitrobenzyl alcohol 41. Reaction of alcohol with NaH in the presence of TBSCl in dry THF provided the TBS ether. This was converted to the corresponding thiophenol derivative by reaction with sodium disulfide, freshly prepared from sodium sulfide and elemental sulfur in ethanolic solution in the presence of NaOH to provide a mixture of the corresponding thiol along with its oxidized disulfide derivative. Oxidation of this mixture by a combination of N-chlorosuccinimide and dilute hydrochloric acid in MeCN afforded the corresponding sulfonyl chloride 42 in moderate yield.

Commercially available 5-hexenylamine 43 was reacted with chiral epoxide 44 providing epoxide opening product 45 (Scheme 2). Reaction of these amines with sulfonyl chloride derivatives 40 and 42 afforded the corresponding diene sulfonamide derivatives 46 and 47. For the synthesis of diene 47, sulfonamide intermediate derived from sulfonyl chloride 42 was subjected to nBu$_4$N$^+$F$^-$ in THF. The resulting alcohol was subjected to O-allylation later on with allyl-test-butylcarbonate in the presence of catalytic Pd(PPh$_3$)$_4$ to provide 47. For the synthesis of the saturated inhibitors with p-OMe and nitrosulfonamides, diene derivatives 46 and 47 were exposed to ring closing olefin metathesis to provide the corresponding unsaturated macrocycles as E/Z mixtures (approximately 1:2 E/Z ratio). Deprotection of Boc-group with TFA was followed by reaction of the resulted amines 48 and 49.

Reaction of amine 48 with activated bis-THF derivative 50 furnished unsaturated inhibitor 51 as a mixture of E/Z isomers (Scheme 3). The mixture of isomers were separated by HPLC using a C18 column to furnish macrocyclic inhibitors. Reaction of amine 49 with a p-NO$_2$ group was converted to E/Z mixture of unsaturated macrocyclic inhibitors 52. Catalytic hydrogenation of 52 over 10% Pd—C provided saturated inhibitor 7. Similarly, reaction of amine 49 with activated carbonate 53 provided the corresponding carbamate which upon catalytic hydrogenation furnished inhibitor 14 (Scheme 4).

Scheme 1.

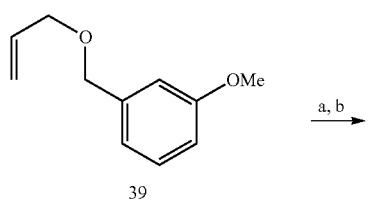

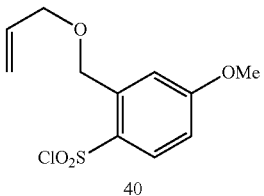

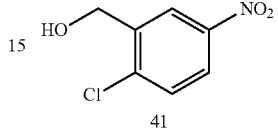

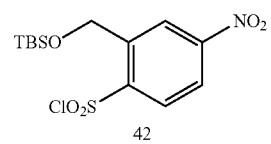

Reagents and conditions: (a) HSO$_3$Cl, CH$_2$Cl$_2$, 0° C., 20 min; (b) cyanuric chloride, Et$_3$N, dry acetone, 23° C. to 60° C., 24 h, 19% over 2 steps; (c) TBSCl, NaH (60% susp. in mineral oil), TBAI, dry THF, 0° C., 1 h, 90%; (d) Na$_2$S$_2$ in EtOH, NaOH, EtOH, reflux, 2 h; (e) NCS, 2M HCl in MeCN, -10° C. to 20° C., 30 min, 35%.

Scheme 2.

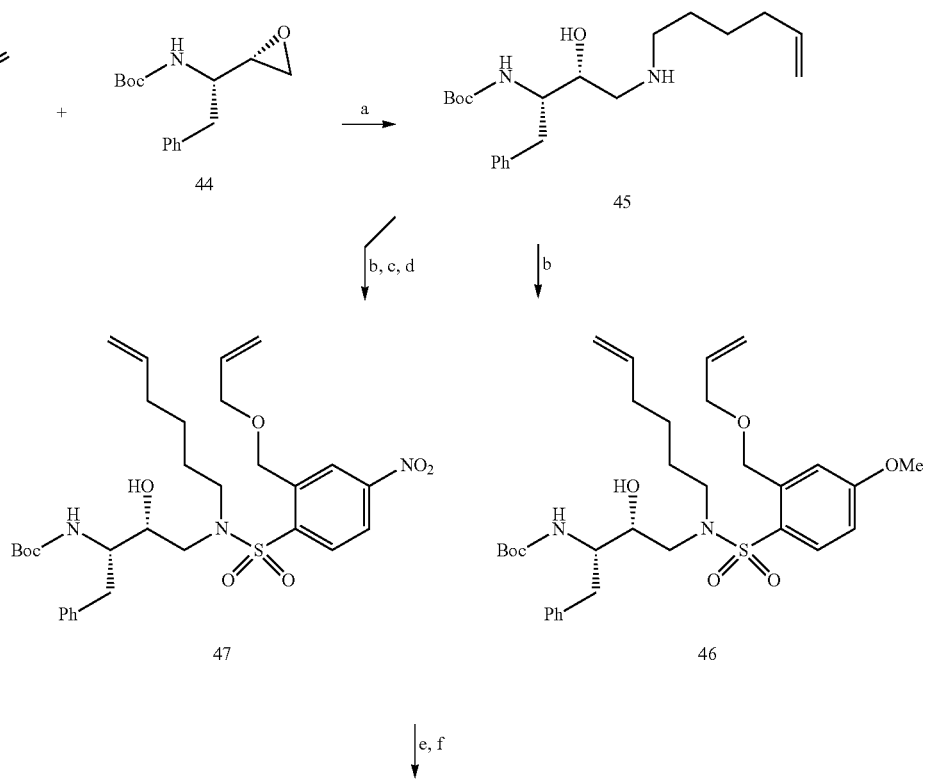

-continued
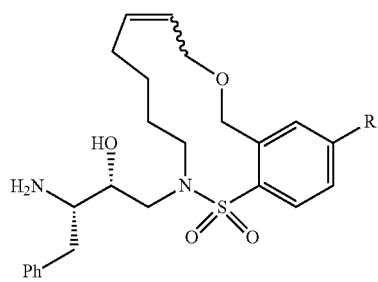
48, R = OMe
49, R = NO₂
Reagents and conditions: (a) iPrOH, 56° C., 14 h, 82%; (b) 40 or 42, aqueous NaHCO₃, CH₂Cl₂, 23° C., 18 h, 80-92%; (c) TBAF, dry THF, 0° C., 15 min, 78%; (d) allyl-tert butylcarbonate, Pd(PPh₃)₄, dry THF, 60° C., 3 h, 72%; (e) Grubbs I, dry CH₂Cl₂, 40° C., 3-6 h, 92-93%; (f) TFA, CH₂Cl₂, 23° C., 3-9 h.
Scheme 3.
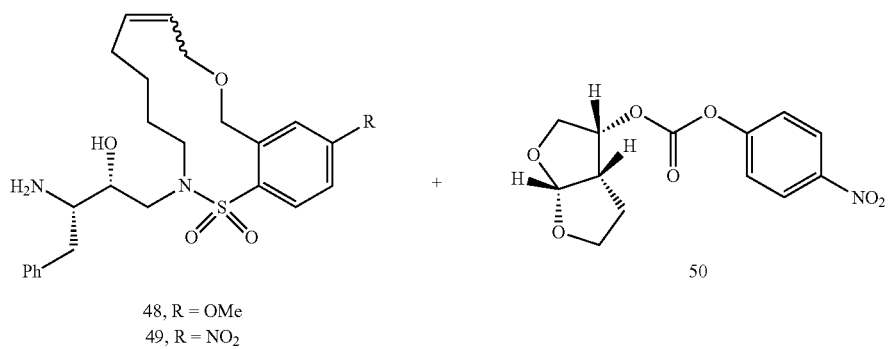
48, R = OMe
49, R = NO₂
50
a ↓
51, R = OMe
52, R = NO₂
b ↓

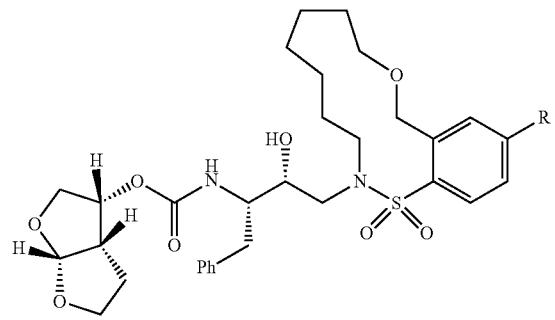

5, R = OMe
7, R = NH₂

Reagents and conditions: (a) DIPEA, MeCN, 23° C., 8 days, 44-49%; (b) H₂, 10% Pd/C, EtOAc, 23° C., 9-12 h, 80-91%.

2-((Allyloxy)methyl)-4-methoxybenzenesulfonyl chloride (40).

Chlorosulfonic acid (0.045 mL, 0.678 mmol) was dissolved in anhydrous CH₂Cl₂ (3 mL) and the solution was cooled to 0° C. and added to a cooled solution of commercially available 1-((allyloxy)methyl)-3-methoxybenzene 39 (110 mg, 0.617 mmol) in anhydrous CH₂Cl₂ (2 mL). The reaction mixture was stirred at 0° C. for 20 min (TLC monitoring). Solvents were evaporated and the residue was purified by silica gel flash chromatography (10-15% MeOH in CH₂Cl₂). The resulting mixture of sulfonic acid isomers 2-((allyloxy)methyl)-4-methoxybenzenesulfonic acid and 4-((allyloxy)methyl)-2-methoxybenzenesulfonic acid (40 mg, 0.155 mmol) was dissolved in dry acetone (8 mL); triethylamine (22 μL, 0.158 mmol) and cyanuric chloride (29 mg, 0.157 mmol) were sequentially added. The reaction mixture was heated to 60° C. and stirred for 24 h. After reaction completion the mixture was allowed to cool to 25° C. and concentrated. The residue was dissolved in EtOAc and filtered through a celite plug. The filtrate was concentrated and purified by silica gel flash chromatography (15-20% EtOAc in n-Hexane) to afford 40 (34 mg, 19% over two steps).

2[((tert-Butyldimethylsilyl)oxy)methyl]-4-nitrobenzenesulfonyl chloride (42).

Commercially available (2-chloro-5-nitrophenyl)methanol 41 (99 mg, 0.528 mmol) was dissolved in dry THF (5 mL) and the resulting solution was cooled to 0° C. Sodium hydride (60% suspension in mineral oil, 53 mg, 1.33 mmol), TBSCl (239 mg, 1.58 mmol) and TBAI (19 mg, 0.052 mmol) were sequentially added at 0° C. and the reaction mixture was stirred for 1 h at 0° C. Reaction mixture was quenched with water and extracted with EtOAc. The combined organic layers were dried on anhydrous Na₂SO₄, filtered, and concentrated under reduced pressure. The crude product was purified by silica gel column chromatography (10% EtOAc in n-Hexane) to afford tert-butyl((2-chloro-5-nitrobenzyl)oxy)dimethylsilane (143 mg, 90%).

A solution of Na₂S₂ was freshly prepared by suspending Na₂S.9H₂O (104 mg, 0.431 mmol) and elemental sulfur (14 mg, 0.431 mmol) in EtOH (10 mL). The yellow mixture was heated to 30° C. until complete dissolution. tert-Butyl((2-chloro-5-nitrobenzyl)oxy)dimethylsilane (99 mg, 0.431 mmol) was dissolved in EtOH (10 mL) and heated to reflux and the Na₂S₂ solution was slowly added. The reaction mixture was refluxed for 2 h, then allowed to cool to 25° C. and poured over ice. After ice melting, the solution was acidified with 2N HCl to pH=2 and then extracted twice with EtOAc. The combined organic layers were dried on anhydrous Na₂SO₄, filtered, and concentrated under reduced pressure. The crude product was purified by silica gel column chromatography (10-15% EtOAc in n-Hexane) providing 2-(((tert-butyldimethylsilyl)oxy) methyl)-4-nitrobenzenethiol along with its oxidized disulfide derivative 1,2-bis(2-(((tert-butyldimethylsilyl)oxy) methyl)-4-nitrophenyl)disulfane. This latter mixture (153 mg, 0.511 mmol) was suspended in MeCN (1.5 mL) and added dropwise to a cooled (−10° C.) solution of NCS (273 mg, 2.04 mmol) dissolved in a 2N solution of HCl in MeCN (0.82 mL). The reaction mixture was then allowed to warm to 20° C. and stirred for 30 min. The reaction mixture was treated with diisopropyl ether and washed with brine. The organic layer was dried on anhydrous Na₂SO₄, filtered, and concentrated under reduced pressure to provide 42 (66 mg, 35%), carried on to the next step without further purification.

tert-Butyl ((2S,3R)-4-(hex-5-en-1-ylamino)-3-hydroxy-1-phenylbutan-2-yl)carbarnate (45).

Commercially available hex-5-en-1-amine 43 (40 mg, 0.403 mmol), was dissolved in iPrOH (2 mL) and known tert-butyl ((S)-1-((S)-oxiran-2-yl)-2-phenylethyl)carbamate 44 (106 mg, 0.403 mmol) was added. The reaction mixture was heated to 56° C. and stirred for 14 h. After reaction completion solvent was evaporated and the crude product was purified by silica gel column chromatography (5% MeOH (1% NH₃) in CH₂Cl₂) providing 45 (119 mg, 82%).

tert-Butyl ((2S,3R)-4-((2-((allyloxy)methyl)-N-(hex-5-en-1-yl)-4-methoxyphenyl)sulfonamido)-3-hydroxy-1-phenylbutan-2-yl)carbamate (46).

A solution of sulfonyl chloride 40 (33 mg, 0.119 mmol) in CH₂Cl₂ (3 mL) was added to a round bottom flask containing amine 45 (47 mg, 0.131 mmol). The resulting biphasic mixture was stirred vigorously at 23° C. for 18 h, then the layers were allowed to separate. The organic layer was dried on anhydrous Na₂SO₄, filtered, and concentrated under reduced pressure. The crude product was purified by silica gel column chromatography (50% EtOAc in n-Hexane) providing 46 (66 mg, 92%).

tert-Butyl ((2S,3R)-4-((2-((allyloxy)methyl)-N-(hex-5-en-1-yl)-4-nitrophenyl)sulfonamido)-3-hydroxy-1-phenylbutan-2-yl)carbamate (47).

A solution of sulfonyl chloride 42 (34 mg, 0.093 mmol) in CH₂Cl₂ (3 mL) was added to a round bottom flask containing amine 45 (28 mg, 0.077 mmol). The resulting biphasic mixture was stirred vigorously at 23° C. for 18 h, then the layers were allowed to separate. The organic layer was dried on anhydrous $Na_2SO_4$, filtered, and concentrated under reduced pressure. The crude product was purified by silica gel column chromatography (40% EtOAc in n-Hexane) providing tert-butyl ((2S,3R)-4-((2-(((tert-butyldimethylsilyl)oxy)methyl)-N-(hex-5-en-1-yl)-4-nitrophenyl)sulfonamido)-3-hydroxy-1-phenylbutan-2-yl)carbamate (42 mg, 80%).

This latter (36 mg, 0.052 mmol) was dissolved in dry THF (2 mL) and the solution cooled to 0° C. TBAF (1M in THF, 57 µL, 0.057 mmol) was added and the reaction mixture was stirred at 0° C. for 15 min then quenched with saturated aqueous $NH_4Cl$ and extracted with EtOAc. The crude product was purified by silica gel column chromatography (30% EtOAc in n-Hexane) providing tert-butyl ((2S,3R)-4-((N-(hex-5-en-1-yl)-2-(hydroxymethyl)-4-nitrophenyl)sulfonamido)-3-hydroxy-1-phenylbutan-2-yl)carbamate (23 mg, 78%). This latter (21 mg, 0.036 mmol), was added to a flame dried round bottom flask. $Pd(PPh_3)_4$ (4.2 mg, 0.0036 mmol, 10 mol %) and allyl-tert-butylcarbonate (7 mg, 0.044 mmol) followed by dry THF (5 were added and the reaction mixture was heated to 60° C. for 3 h. The mixture was then concentrated and the residue was purified by silica gel column chromatography (20% EtOAc in n-Hexane) providing 47 (16 mg, 72%).

2-((2R,3S)-3-Amino-2-hydroxy-4-phenylbutyl)-13-methoxy-2,3,4,5,6,9-hexahydro-11H-benzo[c][1]oxa[5]thia [6]azacyclotridecine 1,1-dioxide (48).

Compound 46 (64 mg, 0.106 mmol) was dissolved in dry $CH_2Cl_2$ (40 mL) and Grubbs I catalyst (9 mg, 0.0109 mmol, 10 mol %) was added to the solution. The reaction mixture was stirred at 40° C. for 4 h and then quenched by adding ethyl vinyl ether and concentrated. The crude product was purified by silica gel column chromatography (25% EtOAc in n-Hexane) providing tert-butyl ((2S,3R)-3-hydroxy-4-(13-methoxy-1,1-dioxido-4,5,6,9-tetrahydro-11H-benzo[c] [1]oxa[5]thia[6]azacyclotridecin-2(3H)-yl)-1-phenylbutan-2-yl)carbamate as E/Z mixture (57 mg, 93%). This latter (10 mg, 0.0173 mmol) was dissolved in $CH_2Cl_2$ (3 mL) and the solution was cooled to 0° C. TFA (200 µL) was added and the reaction mixture was stirred at 25° C. for 3 h. Solvents were evaporated and the residue was taken up with $CH_2Cl_2$ (12 mL), treated with 2 mL of saturated aqueous $NaHCO_3$, dried on anhydrous $Na_2SO_4$, filtered, and concentrated under reduced pressure. The resulting 2-((2R,3S)-3-amino-2-hydroxy-4-phenylbutyl)-13-methoxy-2,3,4,5,6,9-hexahydro-11H-benzo[c][1]oxa[5]thia[6]azacyclotridecine 1,1-dioxide (48) was submitted to the next step without further purification.

(3R,3aS,6a R)-Hexahydrofuro[2,3-b]furan-3-yl ((2S,3R)-3-hydroxy-4-(13-methoxy-1,1-dioxido-4,5,6,9-tetrahydro-11H-benzo[c][1]oxa[5]thia[6]azacyclotridecin-2(3H)-yl)-1-phenylbutan-2-yl)carbamate (51).

Amine 48 (8 mg, 0.0173 mmol) was dissolved in MeCN (2 mL) and N,N-DIPEA (30 µL, 0.173 mmol) followed by known activated bis-THF derivative 50 (5 mg 0.0170 mmol) were added. The reaction mixture was stirred at 25° C. for 8 days, then volatiles were evaporated under reduced pressure and the residue was purified by silica gel column chromatography (40% EtOAc in n-Hexane) providing 51 as E/Z mixture of isomers (4.7 mg, 44%).

(3R,3aS,6aR)-Hexahydrofuro[2,3-b]furan-3-yl ((2S,3R)-3-hydroxy-4-(13-methoxy-1,1-dioxido-4,5,6,7,8,9-hexahydro-11H-benzo[c][1]oxa[5]thia[6]azacyclotridecin-2 (3H)-yl)-1-phenylbutan-2-yl)carbamate (5).

Compound 51 (5 mg, 0.0079 mmol) was dissolved in EtOAc (3 mL) and Pd/C (5 mg) was added. The reaction mixture was stirred under hydrogen atmosphere for 12 h and then filtered on a celite plug. The reaction crude was purified by silica gel column chromatography (EtOAc) providing inhibitor 5 (4 mg, 80%).

$^1$H NMR (400 MHz, $CDCl_3$) δ 7.85 (d, J=8.8 Hz, 1H), 7.47-7.12 (m, 5H), 7.06 (d, J=2.6 Hz, 1H), 6.91 (dd, J=8.8, 2.7 Hz, 1H), 5.65 (d, J=5.2 Hz, 1H), 5.04 (dd, J=14.2, 6.3 Hz, 1H), 4.95 (d, J=8.6 Hz, 1H), 4.92-4.82 (m, 1H), 4.81-4.65 (m, 1H), 4.03-3.77 (m, 8H), 3.76-3.58 (m, 4H), 3.33-3.16 (m, 3H), 3.14-2.97 (m, 2H), 2.96-2.84 (m, 1H), 2.81 (dd, J=14.0, 9.2 Hz, 1H), 1.72-1.46 (m, 6H), 1.45-1.33 (m, 2H), 1.28 (s, 4H). LRMS (ESI) m/z $[M+H]^+$ 633.3, $[M+Na]^+$ 655.2.

2-((2R,3S)-3-Amino-2-hydroxy-4-phenylbutyl)-13-nitro-2, 3,4,5,6,9-hexahydro-11H-benzo[c][1]oxa[5]thia[6]azacyclotridecine 1,1-dioxide (49)

Compound 47 (16 mg, 0.026 mmol) was dissolved in dry $CH_2Cl_2$ (16 mL) and Grubbs I catalyst (5 mg, 0.0060 mmol, 20 mol %) was added to the solution. The reaction mixture was stirred at 40° C. for 3 h and then quenched by adding ethyl vinyl ether and concentrated. The crude product was purified by silica gel column chromatography (40% EtOAc in n-Hexane) providing tert-butyl ((2S,3R)-3-hydroxy-4-(13-nitro-1,1-dioxido-4,5,6,9-tetrahydro-11H-benzo[c][1] oxa[5]thia[6]azacyclotridecin-2(3H)-yl)-1-phenylbutan-2-yl)carbamate as E/Z mixture (14 mg, 92%). This latter (10 mg, 0.0169 mmol) was dissolved in $CH_2Cl_2$ (3 mL) and the solution was cooled to 0° C. TFA (100 µL) was added and the reaction mixture was stirred at 25° C. for 6 h. Solvents were evaporated and the residue was taken up with $CH_2Cl_2$ (12 mL), treated with 2 mL of saturated aqueous $NaHCO_3$, dried on anhydrous $Na_2SO_4$, filtered, and concentrated under reduced pressure. The resulting 2-((2R,3S)-3-amino-2-hydroxy-4-phenylbutyl)-13-nitro-2,3,4,5,6,9-hexahydro-11H-benzo[c][1]oxa[5]thia[6]azacyclotridecine 1,1-dioxide (49) was used to the next step without further purification.

(3R,3aS,6aR)-Hexahydrofuro[2,3-b]furan-3-yl ((2S,3R)-3-hydroxy-4-(13-nitro-1,1-dioxido-4,5,6,9-tetrahydro-11H-benzo[c][1]oxa[5]thia[6]azacyclotridecin-2(3H)-yl)-1-phenylbutan-2-yl)carbamate (52).

Amine 49 (8 mg, 0.0163 mmol) was dissolved in MeCN (4 mL) and N,N-DIPEA (20 µL, 0.161 mmol) was added followed by know activated bis-THF derivative 50 (5 mg, 0.0169 mmol). The reaction mixture was stirred at 25° C. for 5 days, then volatiles were evaporated under reduced pressure and the residue was purified by silica gel column chromatography (20-50% EtOAc in n-Hexane) providing 52 as E/Z mixture of isomers (5 mg, 49%).

(3R,3aS,6aR)-Hexahydrofuro[2,3-b]furan-3-yl ((2S,3R)-4-(13-amino-1,1-dioxido-4,5,6,7,8,9-hexahydro-11H-benzo [c][1]oxa[5]thia[6]azacyclotridecin-2(3H)-yl)-3-hydroxy-1-phenylbutan-2-yl)carbamate (7).

Compound 52 (8 mg, 0.0124 mmol) was dissolved in EtOAc (3 mL) and Pd/C (5 mg) was added. The reaction mixture was stirred under hydrogen atmosphere for 9 h and then filtered on a celite plug. The reaction crude was purified by silica gel column chromatography (EtOAc) providing inhibitor 7 (7 mg, 91%).

$^1$H NMR (400 MHz, $CDCl_3$) δ 7.69 (d, J=8.6 Hz, 1H), 7.32-7.11 (m, 6H), 6.75 (d, J=2.3 Hz, 1H), 6.62 (dd, J=8.6, 2.4 Hz, 1H), 5.65 (d, J=5.2 Hz, 1H), 5.03 (dd, J=14.2, 6.3 Hz, 1H), 4.95 (d, J=8.7 Hz, 1H), 4.90-4.77 (m, 1H), 4.75-4.63 (m, 1H), 4.15 (s, 2H), 4.06-3.78 (m, 4H), 3.70 (dt, J=10.7, 5.7 Hz, 4H), 3.49 (d, J=4.4 Hz, 1H), 3.30-3.16 (m, 2H), 3.14-2.98 (m, 2H), 2.97-2.87 (m, 1H), 2.80 (dd, J=13.9, 9.2 Hz, 1H), 1.75-1.15 (m, 12H). LRMS (ESI) m/z$[M+H]^+$ 618.3, $[M+Na]^+$ 640.3.

Scheme 4.

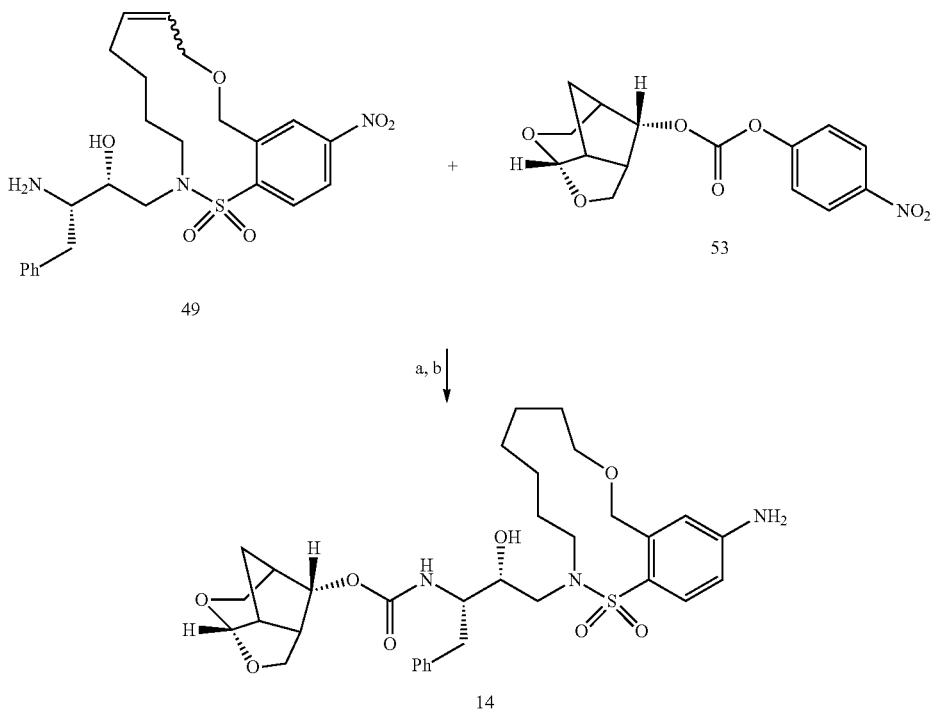

Reagents and conditions: (a) DIPEA, MeCN, 23° C., 2 days; (b) H₂, 10% Pd/C, EtOAc, 23° C., 12 h.

(3S,7aS,8S)-Hexahydro-4H-3,5-methanofuro[2,3-b]pyran-8-yl ((2S,3R)-4-(13-amino-1,1-dioxido-4,5,6,7,8,9-hexahydro-11H-benzo[c][1]oxa[5]thia[6]azacyclotridecin-2(3H)-yl)-3-hydroxy-1-phenylbutan-2-yl)carbamate (14).

Amine 49 (5.8 mg, 0.0119 mmol) was dissolved in MeCN (3 mL) and N,N-DIPEA (16 µL, 0.119 mmol) was added followed by know activated crown-THF derivative 53 (4.2 mg, 0.0131 mmol). The reaction mixture was stirred at 25° C. for 7 days, then volatiles were evaporated under reduced pressure and the residue was purified by silica gel column chromatography (20-50% EtOAc in n-Hexane) providing (3S,7aS,8S)-Hexahydro-4H-3,5-methanofuro[2,3-b]pyran-8-yl ((2S,3R)-3-hydroxy-4-(13-nitro-1,1-dioxido-4,5,6,9-tetrahydro-11H-benzo[c][1]oxa[5]thia[6]azacyclotridecin-2(3H)-yl)-1-phenylbutan-2-yl)carbamate as E/Z mixture of isomers (3.5 mg, 44%). This latter (3.5 mg, 0.0052 mmol) was dissolved in EtOAc (3 mL) and Pd/C (7 mg) was added. The reaction mixture was stirred under hydrogen atmosphere for 10 h and then filtered on a celite plug. The reaction crude was purified by silica gel column chromatography (30-70% EtOAc in n-Hexane) providing 14 (1.6 mg, 48%). $^1$H NMR (800 MHz, CDCl₃) δ 7.70 (d, J=8.0 Hz, 1H), 7.33-7.13 (m, 6H), 6.76 (s, 1H), 6.63 (d, J=8.0 Hz, 1H), 5.42 (d, J=6.4 Hz, 1H), 5.11 (s, 1H), 5.00 (d, J=8.0 Hz, 1H), 4.89-4.81 (m, 2H), 4.73-4.61 (m, 1H), 4.16 (s, 1H), 3.93-3.84 (m, 3H), 3.77 (d, J=9.6 Hz, 1H), 3.69-3.64 (m, 2H), 3.63 (t, J=8.8 Hz, 1H), 3.57 (t, J=7.6 Hz, 1H), 3.28-3.15 (m, 3H), 3.13-3.10 (m, 1H), 3.09-3.02 (m, 1H), 2.88-2.85 (m, 1H), 2.73-2.69 (m, 1H), 2.68-2.64 (m, 1H), 2.37-2.34 (m, 1H), 1.82 (d, J=11.2 Hz, 1H), 1.69-1.15 (m, 11H). LRMS (ESI) m/z [M+H]⁺ 644.2, [M+Na]⁺ 666.3.

The disclosure provides for the following embodiments, the numbering of which is not to be construed as designating levels of importance:

Embodiment 1 relates to a compound of the formula (I):

(I)

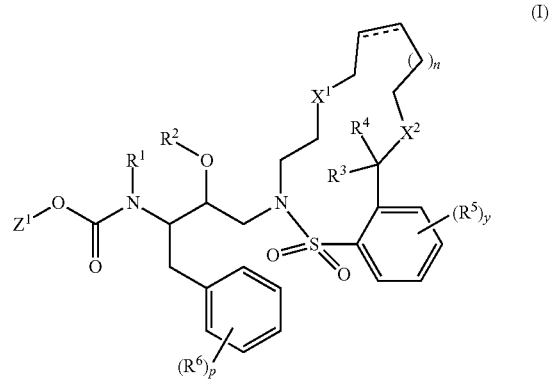

or a pharmaceutically acceptable salt, isomer, mixture of isomers, crystalline form, non crystalline form, hydrate, or solvate thereof wherein:
the dashed line represents an E- or Z-double bond;
Z is:

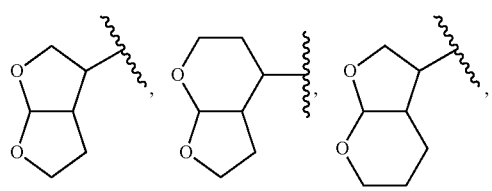

-continued

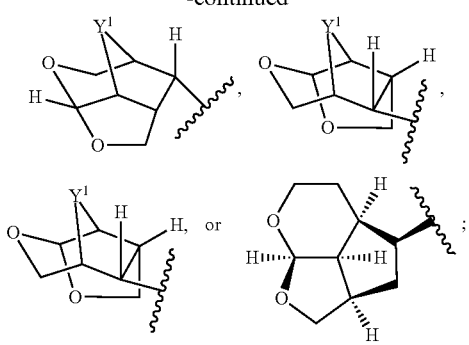

R[1] and R[2] are each independently hydrogen, alkyl or arylalkyl;

R[3] and R[4] are each independently H, alkyl or R[3] and R[4], together with the carbon atom to which they are attached, form a cycloalkyl or a heterocyclyl group;

$Y^1$ is optionally substituted alkylene, O, or N—R$^a$, wherein R$^a$ is hydrogen or alkyl;

$X^1$ and $X^2$ are each independently oxygen, S, S(O), SO$_2$, optionally substituted nitrogen, or optionally substituted alkylene;

each R[5] is independently hydrogen, —OR$^b$, wherein R$^b$ is alkyl or aryl, —SO$_2$R[7], —NR$_2$[7], —CHR[7]OR[7] or CR$_3$[7], wherein each R[7] is independently hydrogen, alkyl, heteroalkyl or heterocyclyl or two adjacent R[5] groups, together with the carbon atoms to which they are attached, form a heteroaryl group;

each R[6] is independently hydrogen, halo, —NR$_2$[7], alkyl, aryl, alkylaryl, heteroalkyl or heterocyclyl;

y is an integer from 1 to 3;

p is an integer from 1 to 3; and n is an integer from 0-4.

Embodiment 2 relates to the compound of Embodiment 1, wherein each R[5] is independently hydrogen, —OR$^b$, wherein R$^b$ is alkyl or aryl or —NR$_2$[7], wherein each R[7] is independently hydrogen, alkyl, heteroalkyl or heterocyclyl.

Embodiment 3 relates to the compound of Embodiment 1, wherein the compound of the formula (I) is a compound of the formula (Ia):

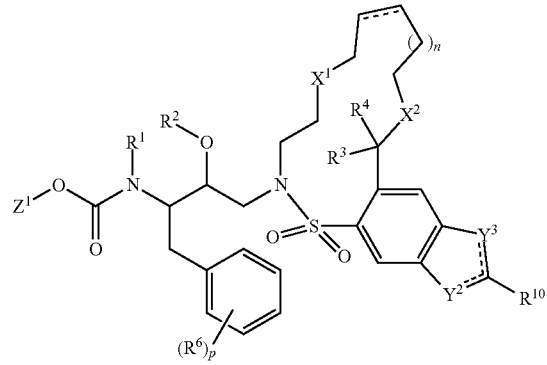

or a pharmaceutically acceptable salt, isomer, mixture of isomers, crystalline form, non crystalline form, hydrate, or solvate thereof wherein:

the dashed line represents an E- or Z-double bond;

$Z^1$ is:

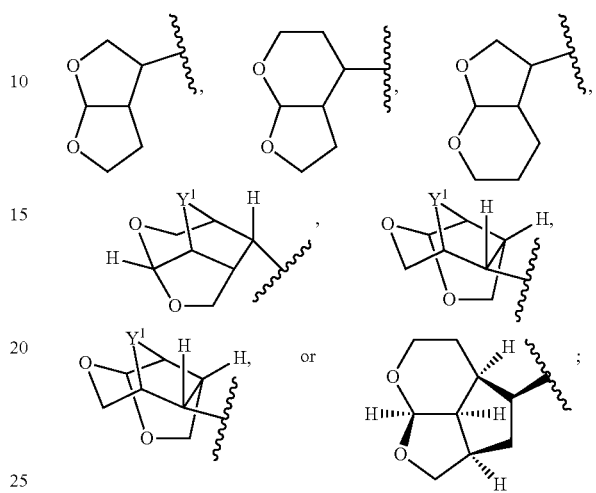

R[1] and R[2] are each independently hydrogen, alkyl or arylalkyl;

R[3] and R[4] are each independently H, alkyl or R[3] and R[4], together with the carbon atom to which they are attached, form a cycloalkyl or a heterocyclyl group;

$Y^1$ is optionally substituted alkylene, O, or N—R$^a$, wherein R$^a$ is hydrogen or alkyl;

$X^1$ and $X^2$ are each independently oxygen, S, S(O), SO$_2$, optionally substituted nitrogen, or optionally substituted alkylene;

each R[6] is independently hydrogen, halo, —NR$_2$[7], alkyl, aryl, alkylaryl, heteroalkyl or heterocyclyl;

R[10] is —OR[9] or —NR$_2$[9], wherein each R[9] is independently hydrogen, alkyl, cycloalkyl, heteroalkyl or heterocyclyl;

$Y^2$ and $Y^3$ are each independently NH, S, O, NR[9] or CR$_2$[11], wherein each R[11] is independently hydrogen, alkyl, aryl, or heterocyclyl;

p is an integer from 1 to 3; and n is an integer from 0-4.

Embodiment 4 relates to the compound of Embodiments 1-3, wherein $Z^1$ is:

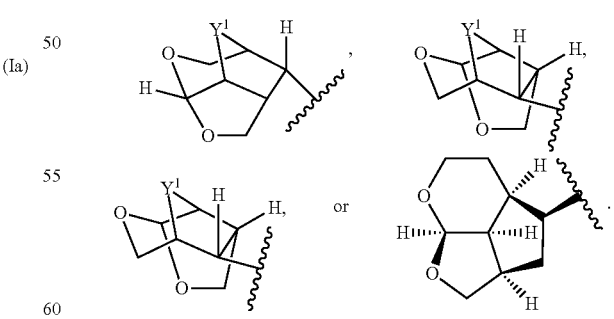

Embodiment 5 relates to the compound of Embodiments 1-4, wherein $Y^1$ is optionally substituted alkylene.

Embodiment 6 relates to the compound of Embodiments 1-5, wherein $Y^1$ is —(CH$_2$)$_m$-Q-, wherein m is an integer from 1-3 and Q is O or N—R$^a$, wherein R$^a$ is hydrogen or alkyl.

Embodiment 7 relates to the compound of Embodiments 1-6, wherein $Y^1$ is —CH$_2$—.

Embodiment 8 relates to the compound of Embodiment 1, wherein the compound of the formula (I) is a compound of the formula (Ib):

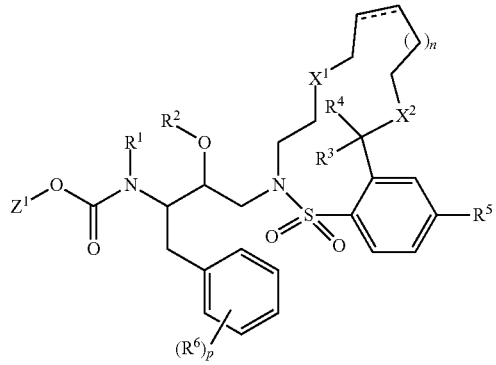

(Ib)

or a pharmaceutically acceptable salt, isomer, mixture of isomers, crystalline form, non crystalline form, hydrate, or solvate thereof wherein:
the dashed line represents an E- or Z-double bond;
$Z^1$ is:

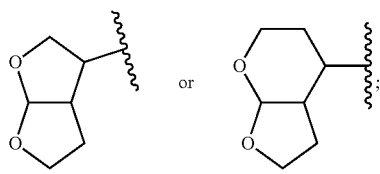 [SMILES: *C1COC2OCCC12 ; *C1CCOC2OCCC12]

$R^1$ and $R^2$ are each independently hydrogen, alkyl or arylalkyl;
$R^3$ and $R^4$ are each independently H, alkyl or $R^3$ and $R^4$, together with the carbon atom to which they are attached, form a cycloalkyl or a heterocyclyl group;
$X^1$ and $X^2$ are each independently oxygen, S, S(O), SO$_2$, optionally substituted nitrogen, or optionally substituted alkylene;
$R^5$ is hydrogen, —OR$^b$, wherein R$^b$ is alkyl or aryl, —SO$_2$R$^7$, —NR$_2^7$, —CHR$^7$OR$^7$ or CR$_3^7$, wherein each R$^7$ is independently hydrogen, alkyl, heteroalkyl or heterocyclyl or two adjacent R$^5$ groups, together with the carbon atoms to which they are attached, form a heteroaryl group;
each R$^6$ is independently hydrogen, halo, —NR$_2^7$, alkyl, aryl, alkylaryl, heteroalkyl or heterocyclyl;
p is an integer from 1 to 3; and
n is an integer from 0-4.

Embodiment 9 relates to a compound of the formula (II):

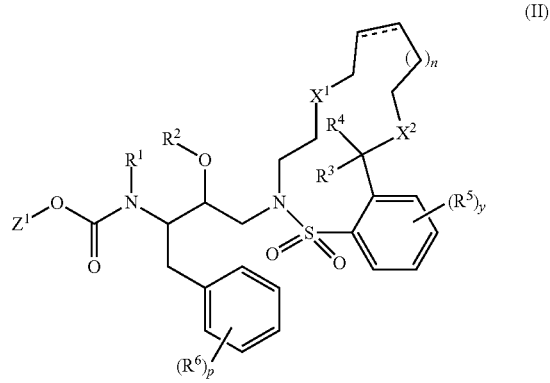

(II)

or a pharmaceutically acceptable salt, isomer, mixture of isomers, crystalline form, non crystalline form, hydrate, or solvate thereof wherein: the dashed line represents an E- or Z-double bond;
$Z^2$ is:

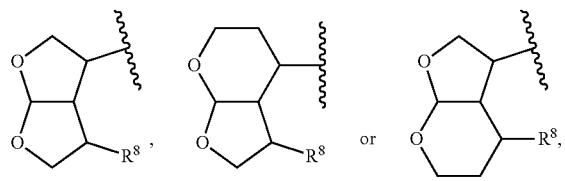

wherein R$^8$ is —OR$^9$ or —NR$_2^9$, wherein each R$^9$ is independently hydrogen, alkyl, heteroalkyl or heterocyclyl;
$R^1$ and $R^2$ are each independently hydrogen, alkyl or arylalkyl;
$R^3$ and $R^4$ are each independently H, alkyl or $R^3$ and $R^4$, together with the carbon atom to which they are attached, form a cycloalkyl or a heterocyclyl group;
$X^1$ and $X^2$ are each independently oxygen, S, S(O), SO$_2$, optionally substituted nitrogen, or optionally substituted alkylene;
each R$^5$ is independently hydrogen, —OR$^b$, wherein R$^b$ is alkyl or aryl, —SO$_2$R$^7$, —NR$_2^7$, —CHR$^7$OR$^7$ or CR$_3^7$, wherein each R$^7$ is independently hydrogen, alkyl, heteroalkyl or heterocyclyl or two adjacent R$^5$ groups, together with the carbon atoms to which they are attached, form a heteroaryl group; each R$^6$ is independently hydrogen, halo, —NR$_2^7$, alkyl, aryl, alkylaryl, heteroalkyl or heterocyclyl;
y is an integer from 1 to 3;
p is an integer from 1 to 3; and
n is an integer from 0-4.

Embodiment 10 relates to the compound of Embodiment 9, wherein each R$^5$ is independently hydrogen, —OR$^b$, wherein R$^b$ is alkyl or aryl, or —NR$_2^7$, wherein each R$^7$ is independently hydrogen, alkyl, heteroalkyl or heterocyclyl.

Embodiment 11 relates to the compound of Embodiment 9, wherein each R$^5$ is independently hydrogen, —OR$^b$, wherein R$^b$ is alkyl, or —NR$_2^7$, wherein each R$^7$ is independently hydrogen, alkyl, heteroalkyl or heterocyclyl.

Embodiment 12 relates to the compound of Embodiments 1-11, wherein $R^1$ and $R^2$ are each hydrogen.

Embodiment 13 relates to the compound of Embodiments 1-12, wherein $X^1$ and $X^2$ are each independently oxygen, S, $SO_2$ or optionally substituted alkylene.

Embodiment 14 relates to the compound of Embodiments 1-13, wherein $R^3$ and $R^4$ are each hydrogen.

Embodiment 15 relates to the compound of Embodiments 1-14, wherein y is 1.

Embodiment 16 relates to the compound of Embodiments 1-15, wherein p is 1 or 2.

Embodiment 17 relates to the compound of Embodiments 1-16, wherein n is an integer from 1-4.

Embodiment 18 relates to a compound of the formula:

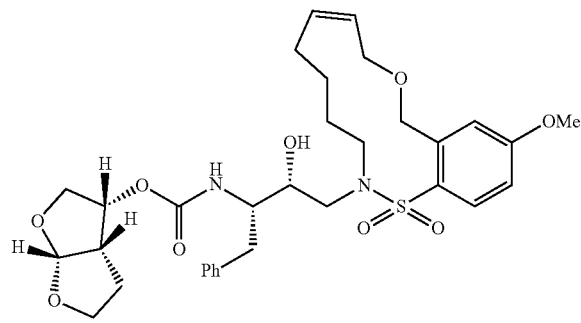

1

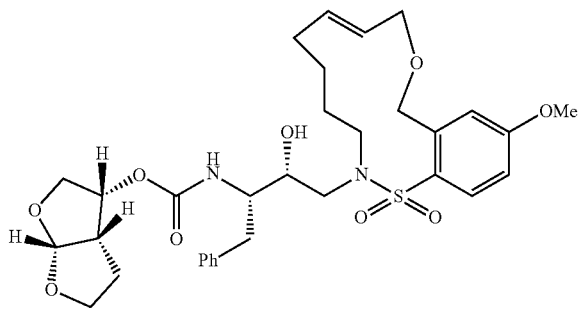

2

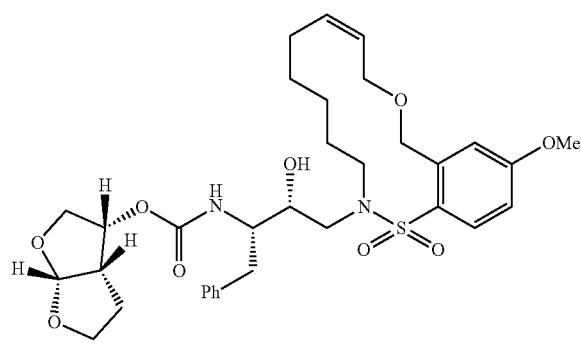

3

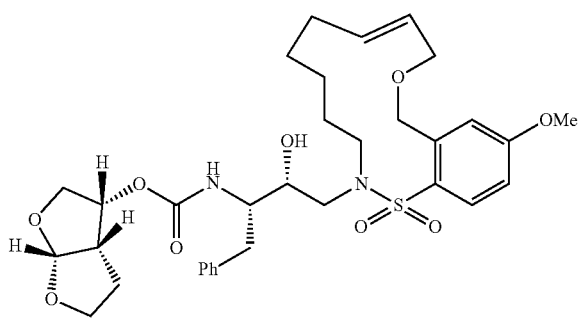

4

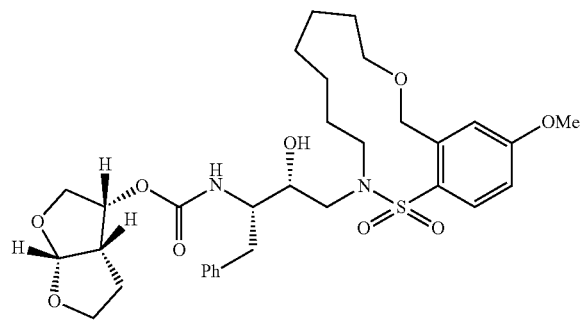

5

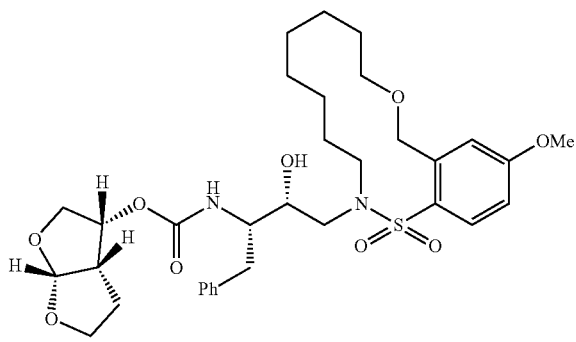

6

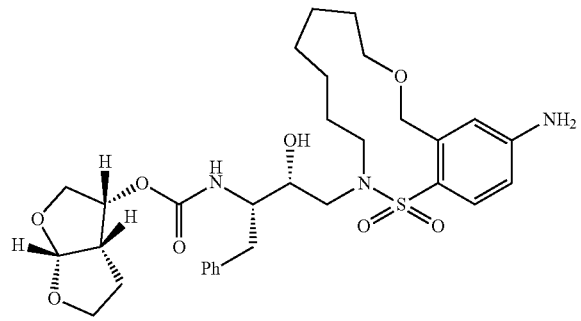

7

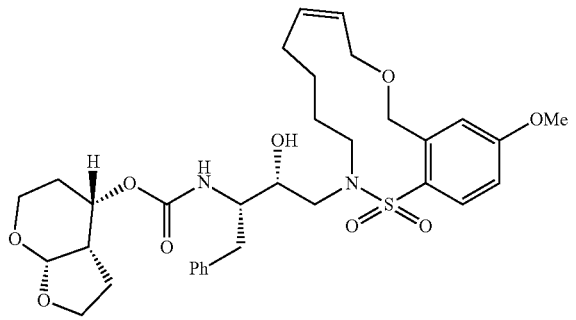

8

-continued
9
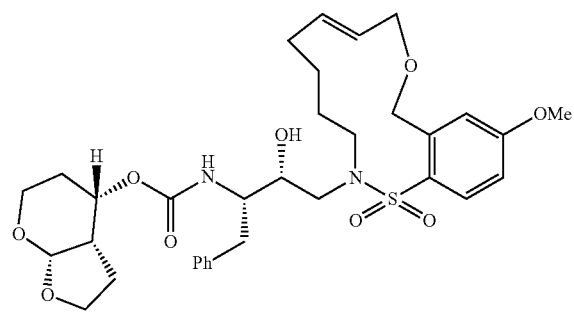
10
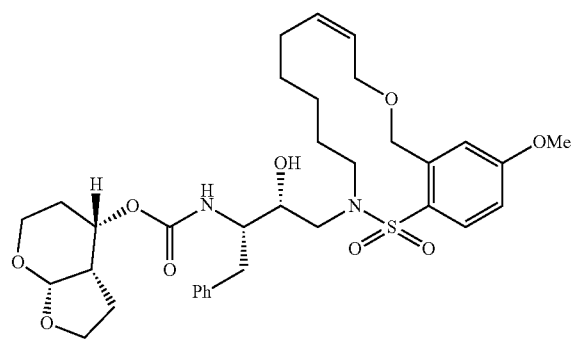
11
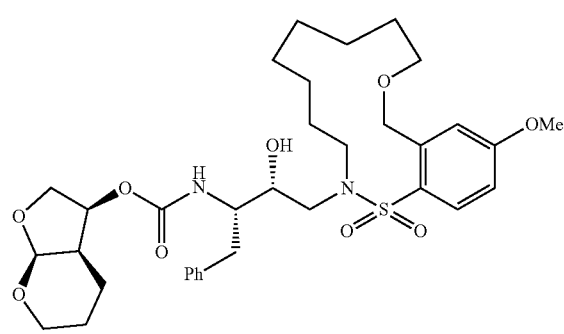
12
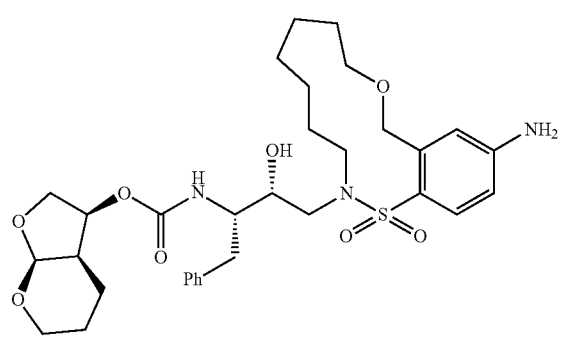
13
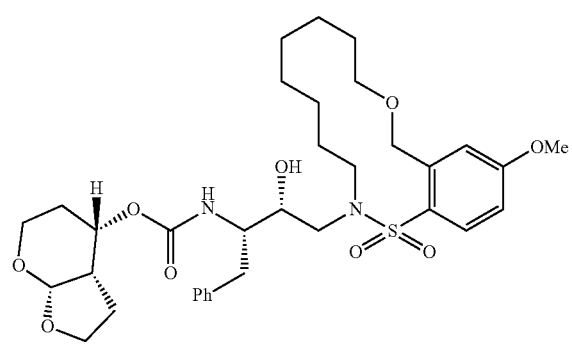
14
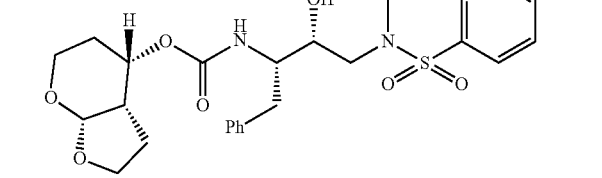
15
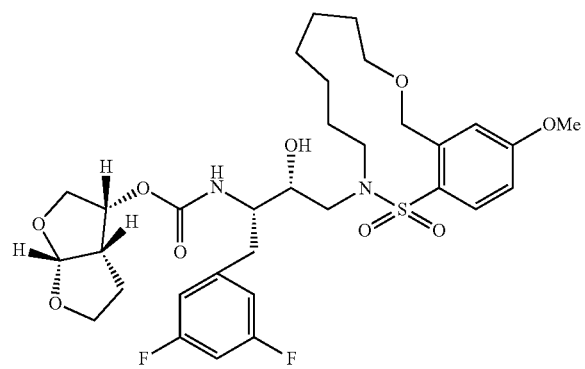
16
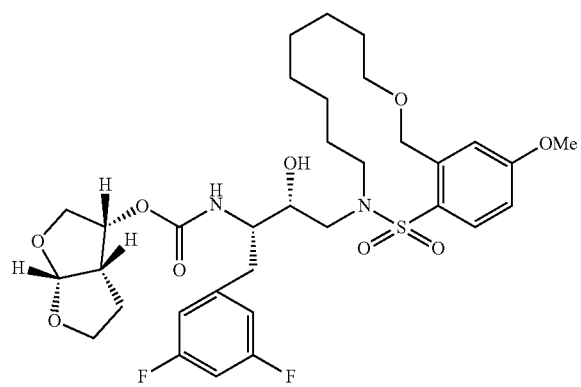

-continued
| 17 | 18 |
|---|---|
| 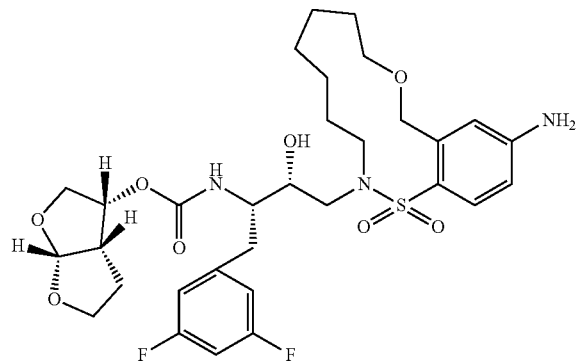 | 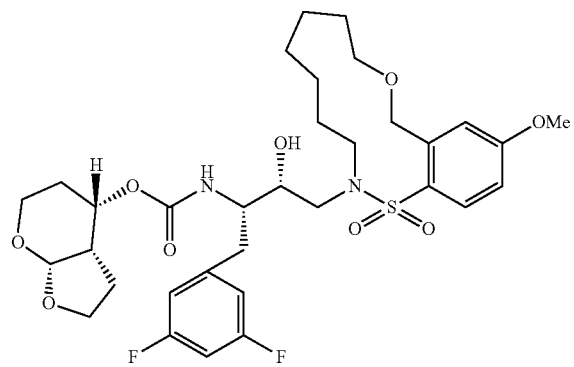 |
| 19 | 20 |
|---|---|
| 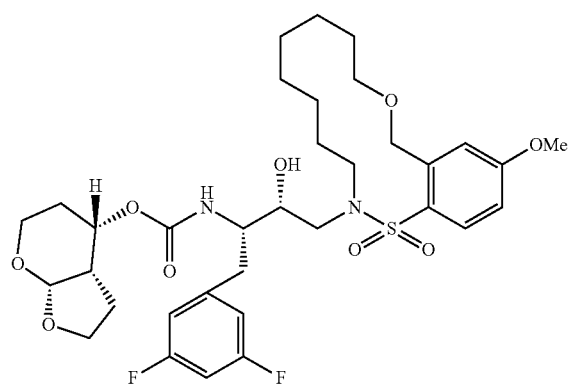 | 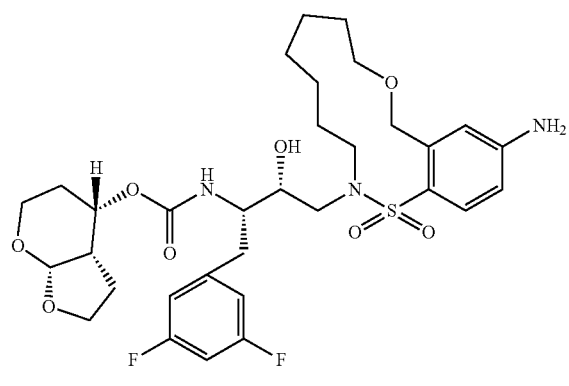 |
| 21 | 22 |
|---|---|
| 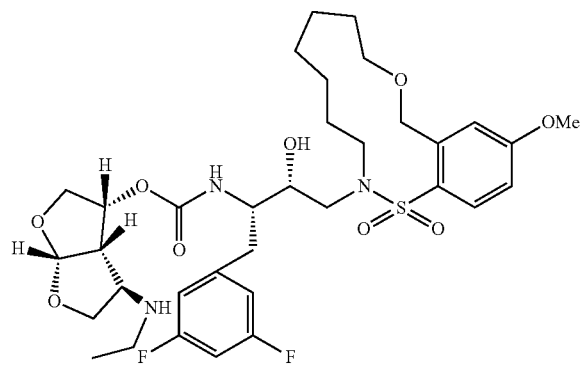 | 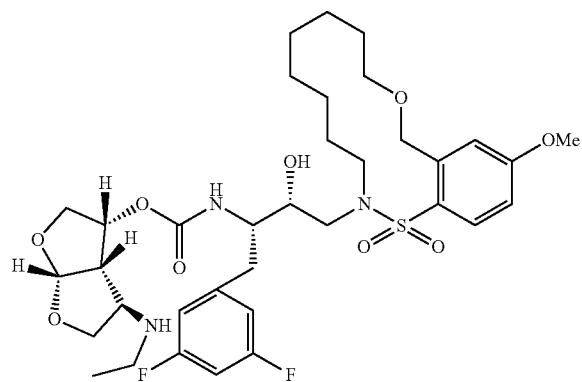 |
| 23 | 24 |
|---|---|
| 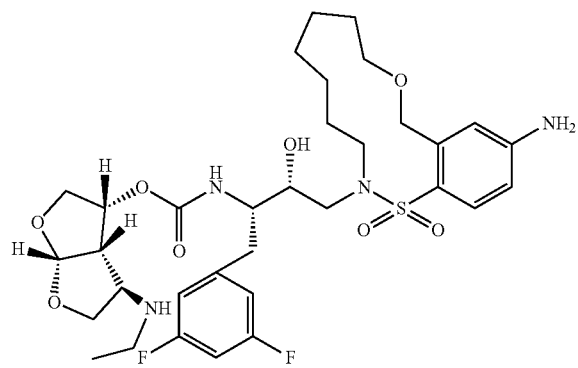 | 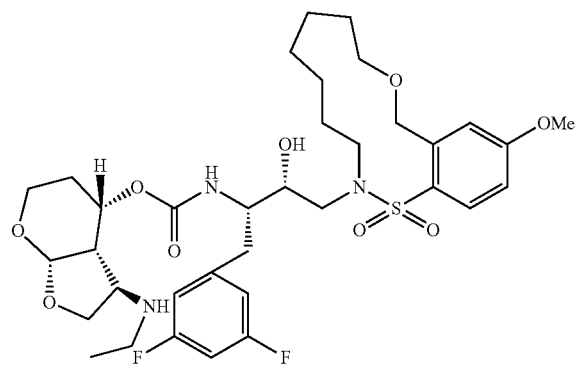 |

-continued
25
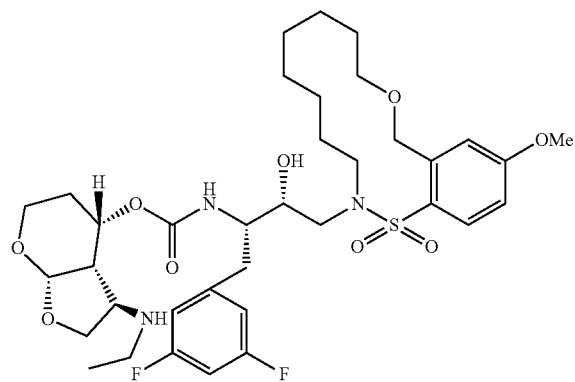
26
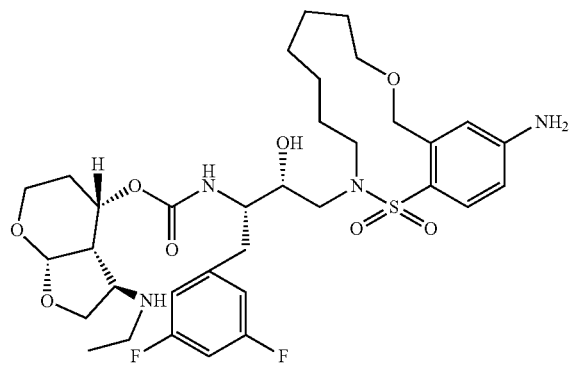
27
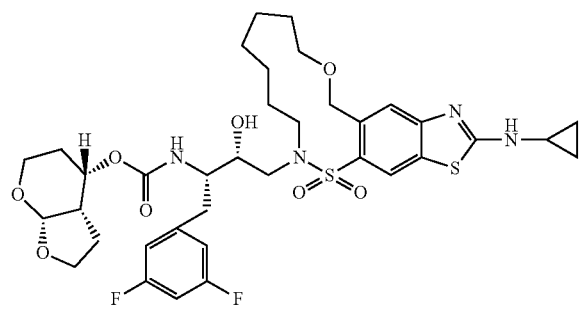
28
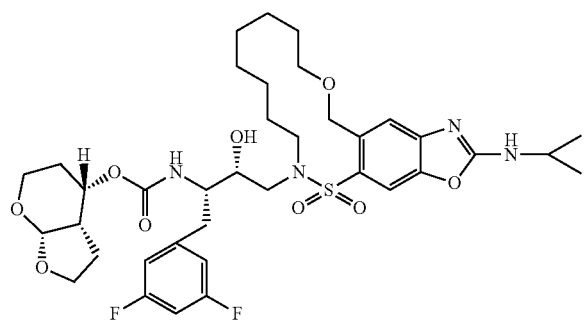
29
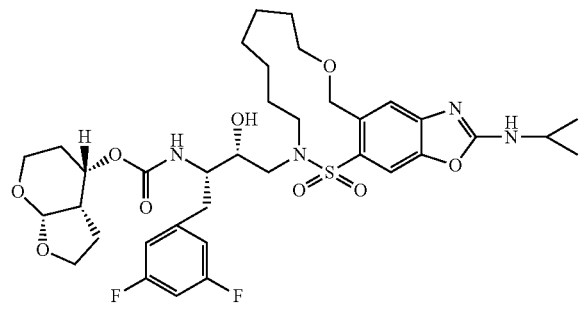
30
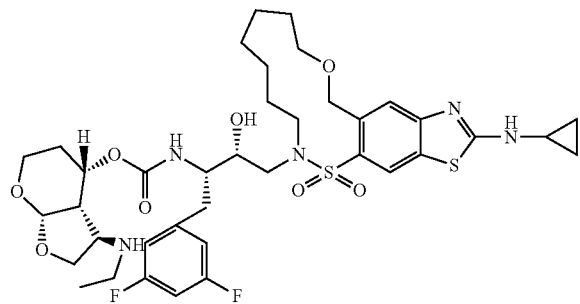
31
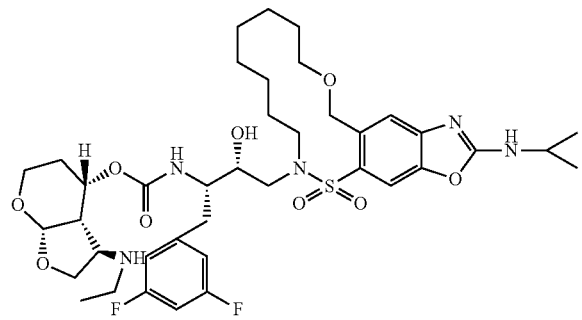
32
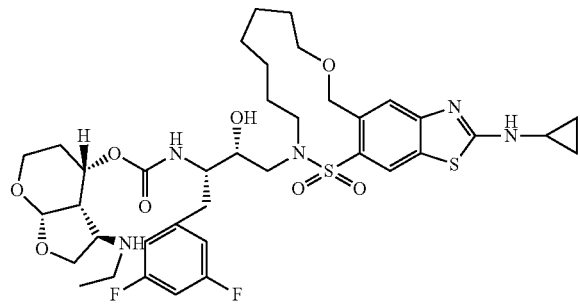

33
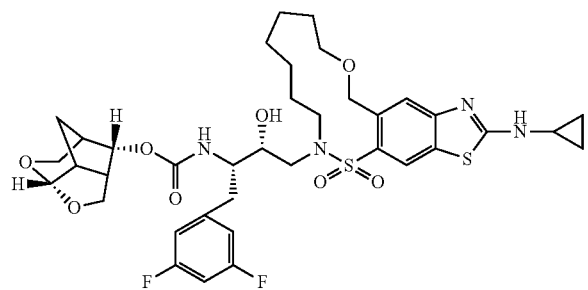
34
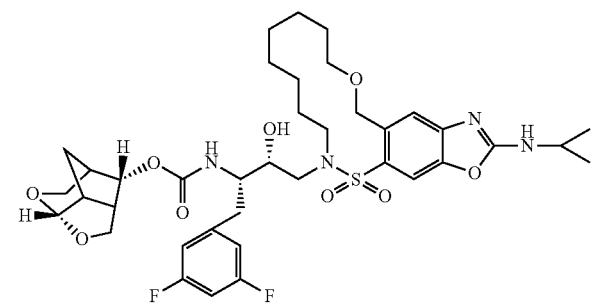
35
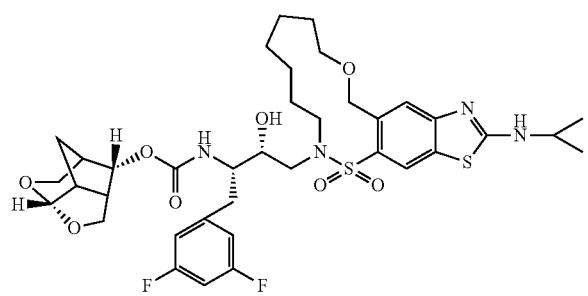
36
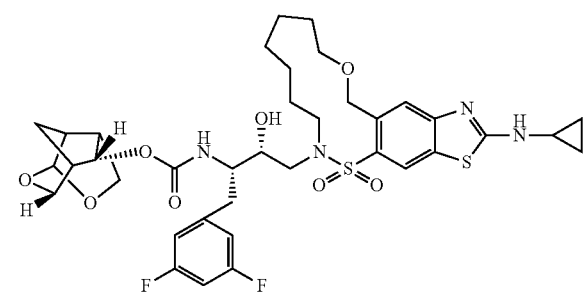
37
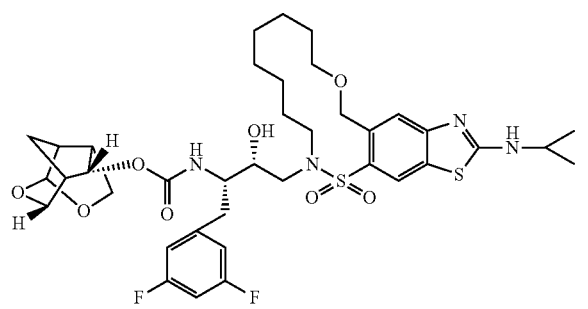
38
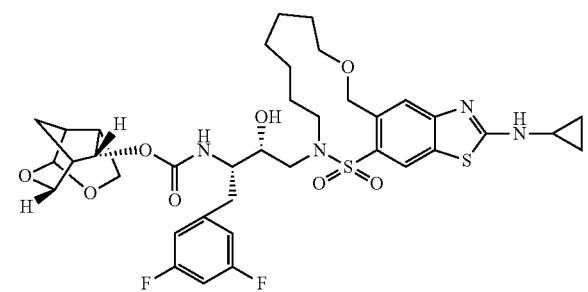
54
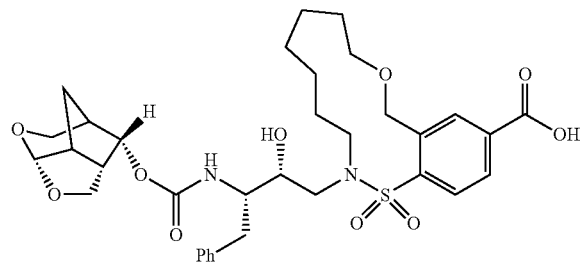
55
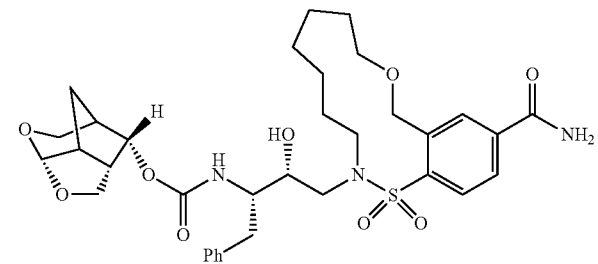
56
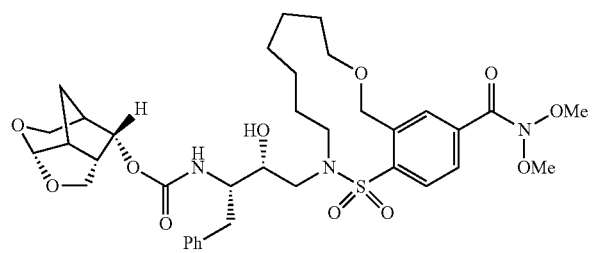
57
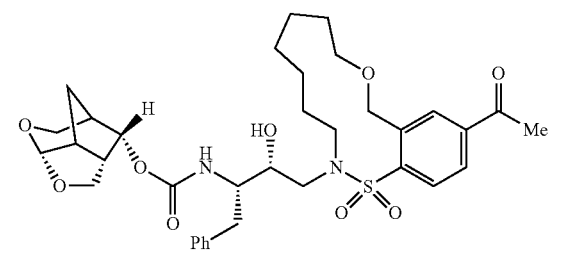

-continued
58
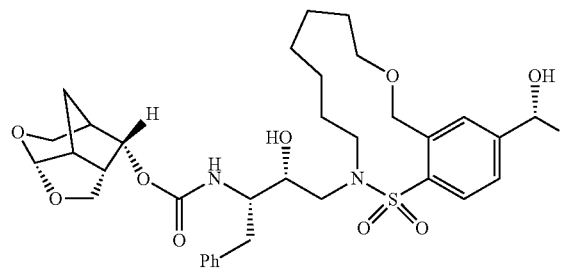
59
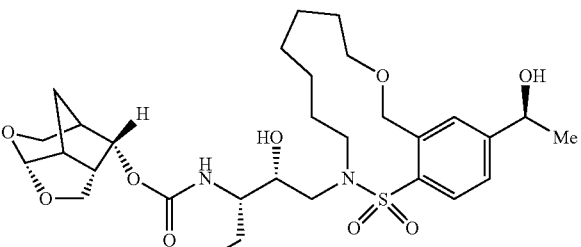
60
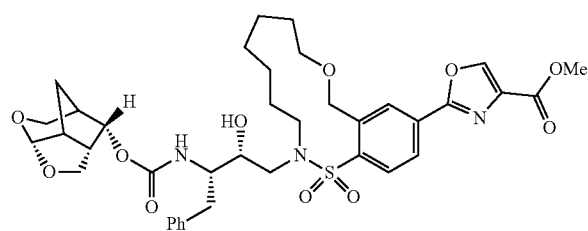
61
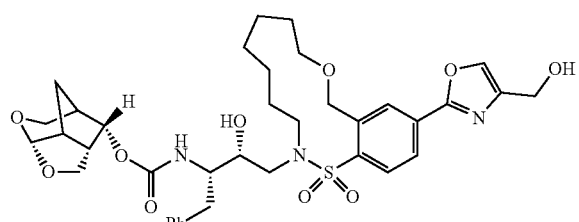
62
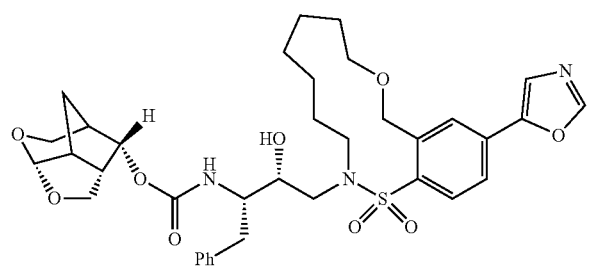
63
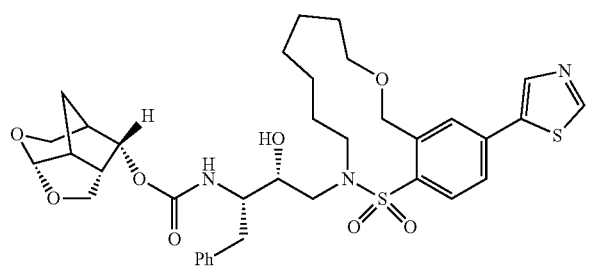
64
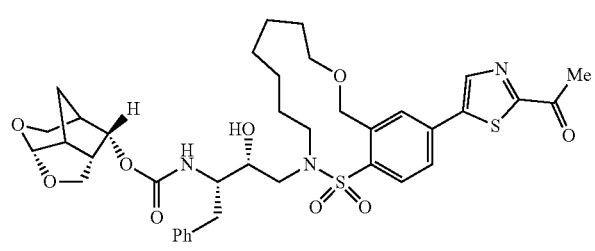
65
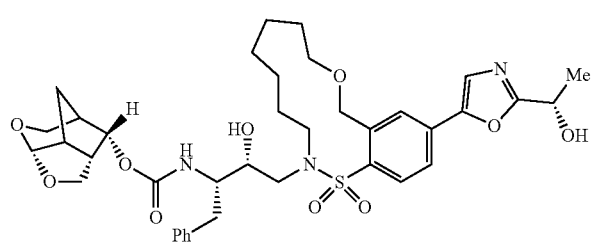
66
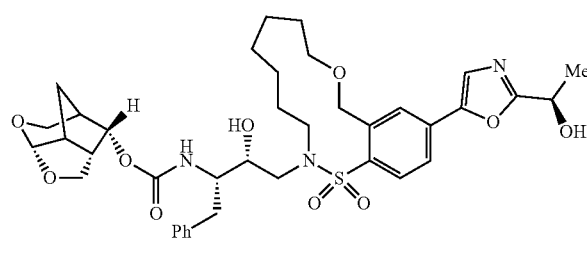
67
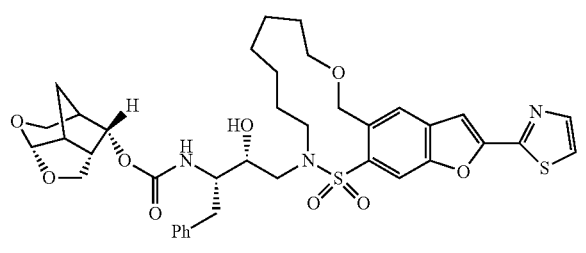
68
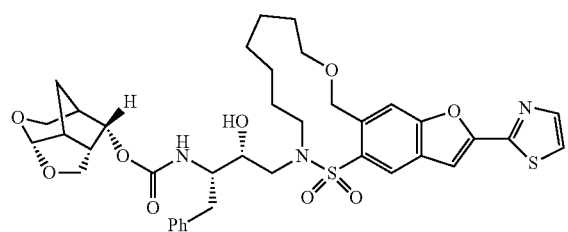
69
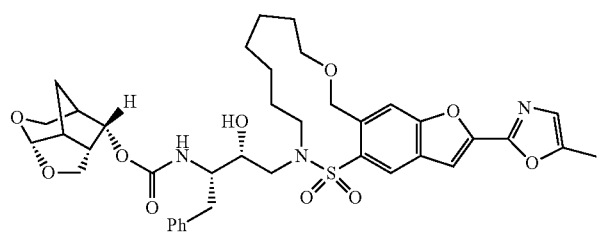

-continued
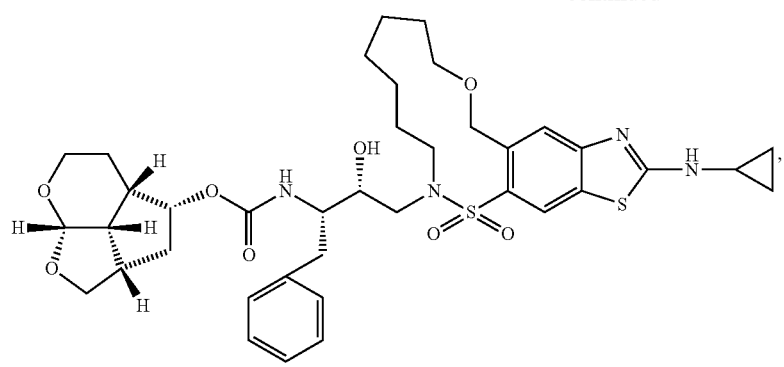
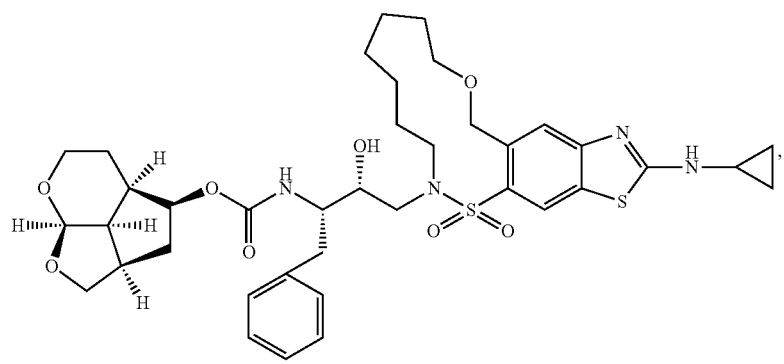
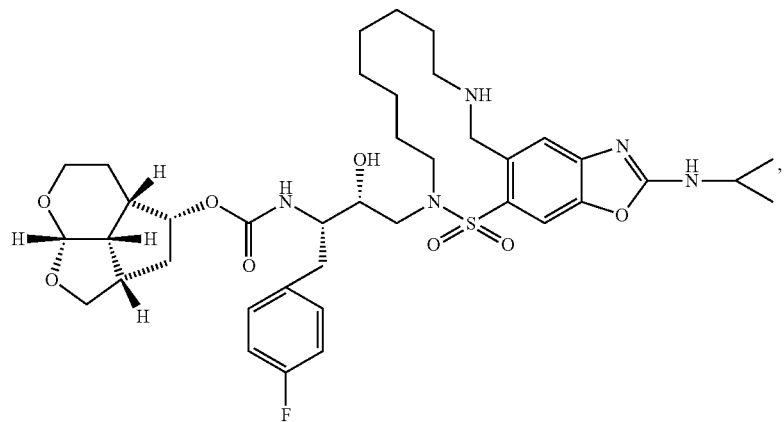
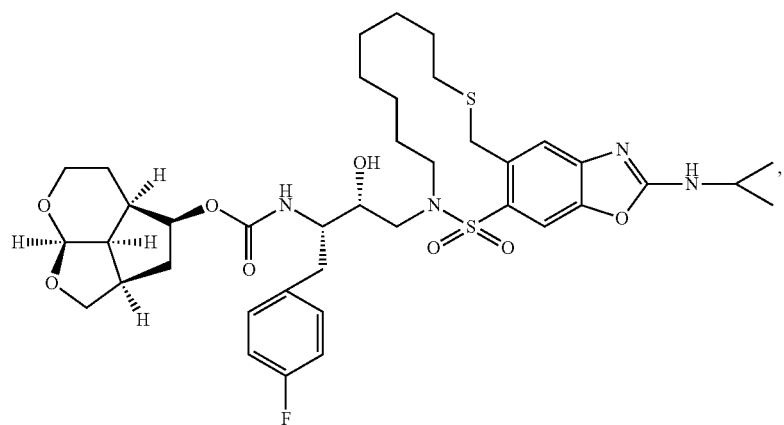

-continued
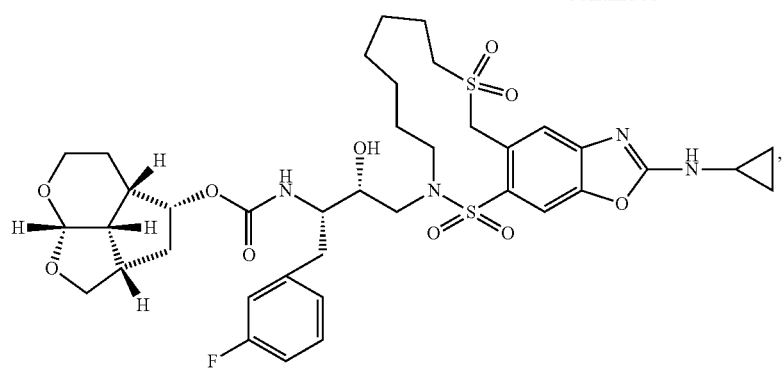
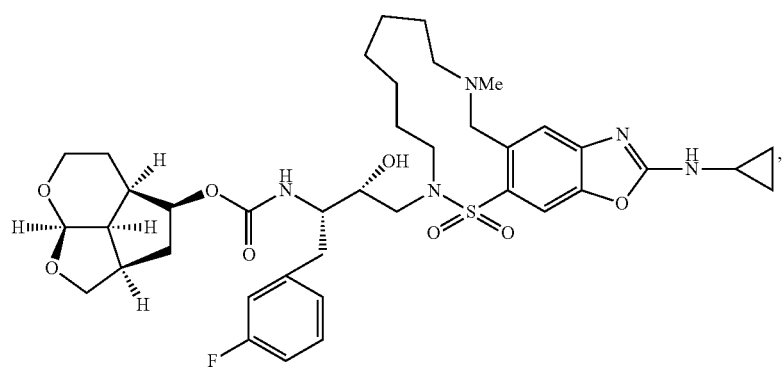
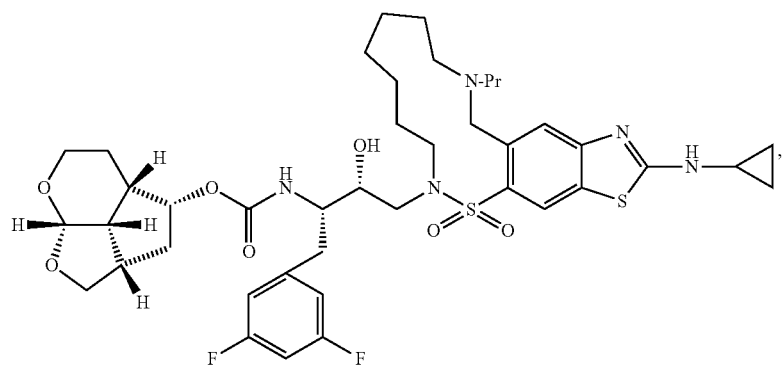
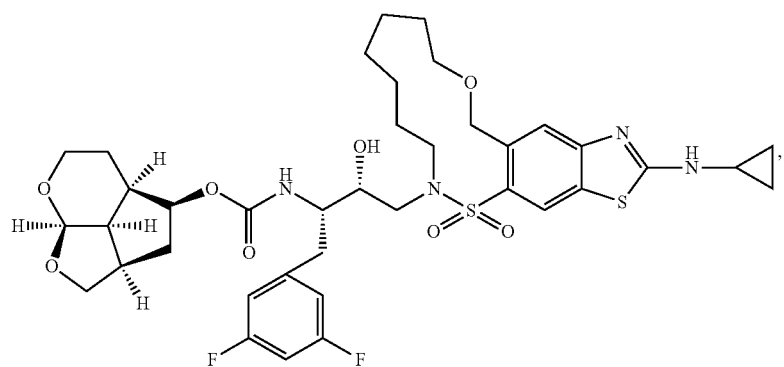

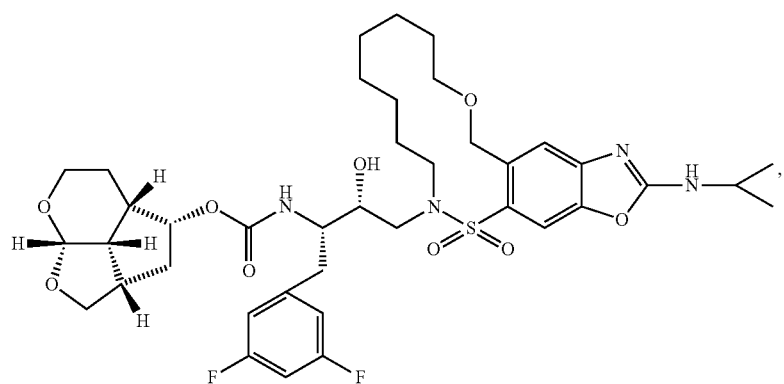
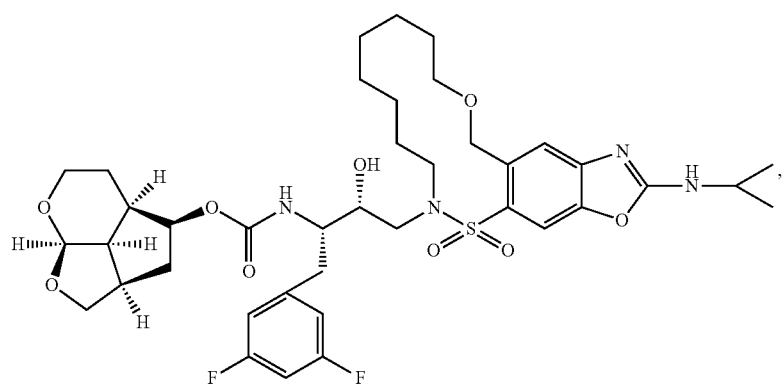
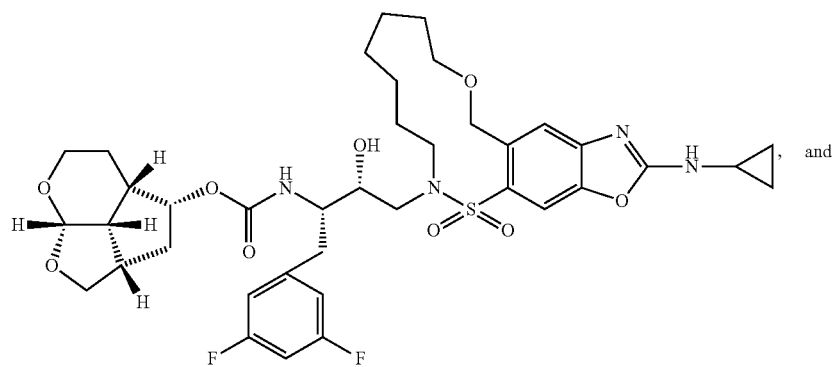, and
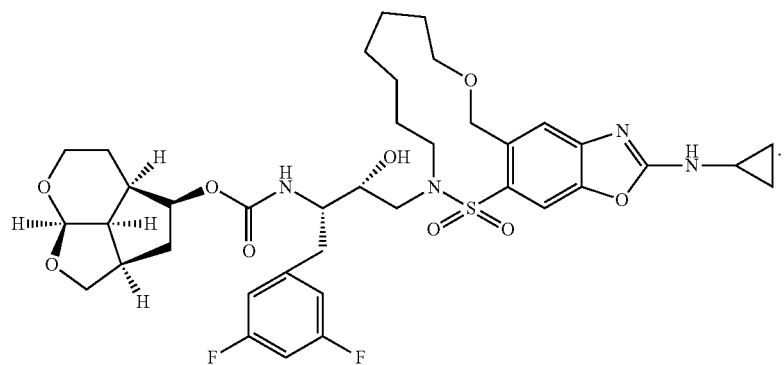

Embodiment 19 relates to a pharmaceutical composition comprising one or more compounds of any one of Embodiments 1-18 and one or more pharmaceutically acceptable carriers, diluents, excipients or combinations thereof.

Embodiment 20 relates to a method for treating a patient in need of relief from HIV/AIDS, the method comprising the step of administering to the patient a therapeutically effective amount of a compound of any one of Embodiments 1-18 or a pharmaceutical composition of Embodiment 19.

What is claimed is:

1. A compound of the formula (I):

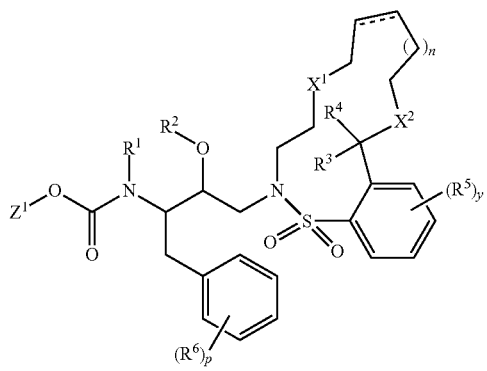

or a pharmaceutically acceptable salt, stereoisomer, crystalline form, non-crystalline form, hydrate, or solvate thereof wherein:

the dashed line represents an E- or Z-double bond;

$Z^1$ is:

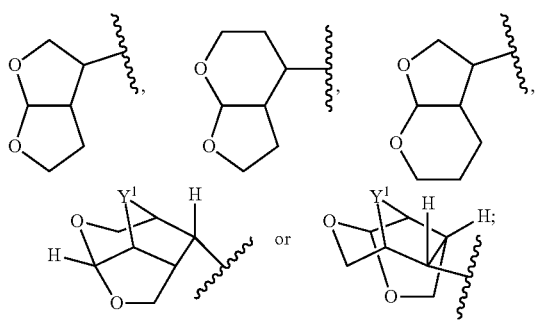

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$Y^1$ is —$CH_2$—;

$X^1$ and $X^2$ are each independently oxygen, $SO_2$, optionally substituted nitrogen, or optionally substituted alkylene;

each $R^5$ is independently hydrogen —$SO_2R^7$, —$NR_2^7$, —$CHR^7OR^7$ or —$CR_3^7$, wherein each $R^7$ is independently hydrogen, heteroalkyl or heterocyclyl or two adjacent $R^5$ groups, together with the carbon atoms to which they are attached, form a heteroaryl group;

each $R^6$ is independently hydrogen, halo, —$NR_2^7$, alkyl, aryl, alkylaryl, heteroalkyl or heterocyclyl;

y is an integer from 1 to 3;

p is an integer from 1 to 3, and n is an integer from 0 to 4.

2. The compound of claim 1, wherein the compound of the formula (I) is a compound of the formula (Ia):

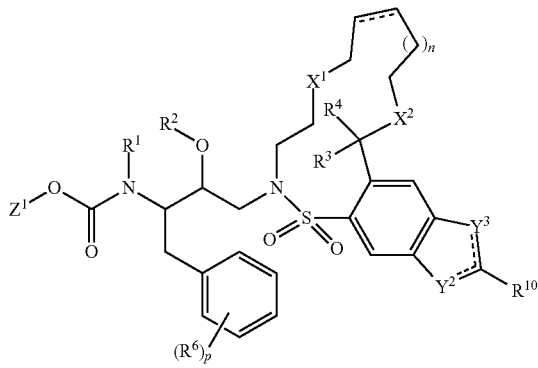

or a pharmaceutically acceptable salt, stereoisomer, crystalline form, non-crystalline form, hydrate, or solvate thereof wherein:

the dashed line represents an E- or Z-double bond;

$Z^1$ is:

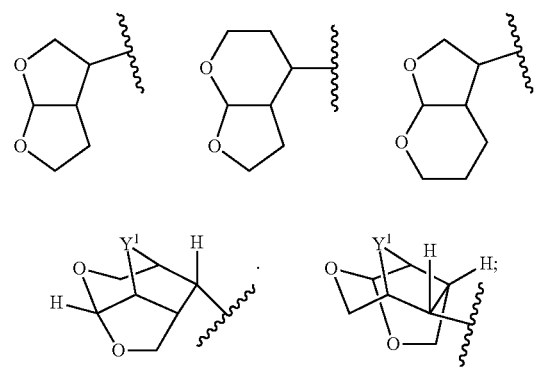

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$Y^1$ is —$CH_2$—;

$X^1$ and $X^2$ are each independently oxygen, $SO_2$, optionally substituted nitrogen, or optionally substituted alkylene;

each $R^6$ is independently hydrogen, halo, —$NR_2^7$, alkyl, aryl, alkylaryl, heteroalkyl or heterocyclyl;

$R^{10}$ is —$OR^9$ or —$NR_2^9$, wherein each $R^9$ is independently hydrogen, alkyl, cycloalkyl, heteroalkyl or heterocyclyl;

$Y^2$ and $Y^3$ are each independently N, S, O, $NR^9$ or $CR^{11}$, wherein each $R^{11}$ is independently hydrogen, alkyl, aryl, or heterocyclyl;

p is an integer from 1 to 3; and n is an integer from 0 to 4.

3. The compound of claim 1, wherein the compound of the formula (I) is a compound of the formula (Ib):

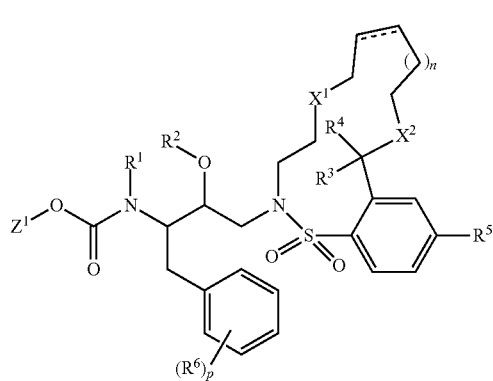

(Ib)

or a pharmaceutically acceptable salt, stereoisomer, crystalline form, non-crystalline form hydrate, or solvate thereof wherein:

the dashed line represents an E- or Z-double bond;

$Z^1$ is:

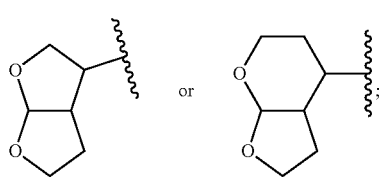 [SMILES: *C1COC2OCCC12 ; *C1CCOC2OCCC12]

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, $SO_2$, optionally substituted nitrogen, or optionally substituted alkylene;

$R^5$ is hydrogen, $-SO_2^7$, $NR_2^7$, $-CHR^7OR^7$ or $CR_3^7$, wherein each $R^7$ is independently hydrogen, heteroalkyl or heterocyclyl or two adjacent $R^5$ groups, together with the carbon atoms to which they are attached, form a heteroaryl group;

each $R^6$ is independently hydrogen, halo, $-NR_2^7$, alkyl, aryl, alkylaryl, heteroalkyl or heterocyclyl;

p is an integer from 1 to 3; and n is an integer from 0 to 4.

4. A compound of the formula (II):

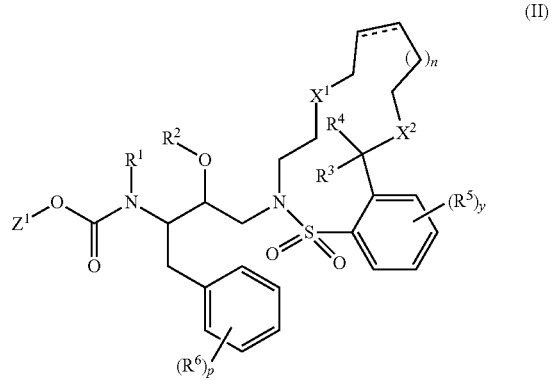

(II)

or a pharmaceutically acceptable salt, stereoisomer, crystalline form, non-crystalline form, hydrate, or solvate thereof wherein:

the dashed line represents an E- or Z-double bond;

$Z^2$ is:

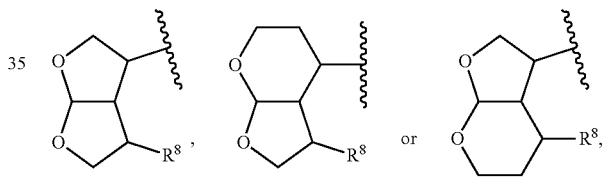

wherein $R^8$ is $-OR^9$ or $-NR_2^9$, wherein each $R^9$ is independently hydrogen, alkyl, heteroalkyl or heterocyclyl;

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, $SO_2$, optionally substituted nitrogen, or optionally substituted alkylene;

each $R^5$ is independently hydrogen, $-SO_2R^7$, $-NR_2^7$, $-CHR^7OR^7$ or $CR_3^7$, wherein each $R^7$ is independently hydrogen, heteroalkyl or heterocyclyl or two adjacent $R^5$ groups, together with the carbon atoms to which they are attached, form a heteroaryl group;

each $R^6$ is independently hydrogen, halo, $-NR_2^7$, alkyl, aryl, alkylaryl, heteroalkyl or heterocyclyl;

y is an integer from 1 to 3;

p is an integer from 1 to 3; and n is an integer from 0 to 4.

5. A compound of the formula:
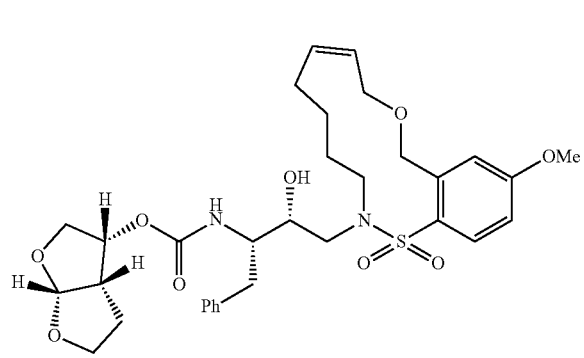
1
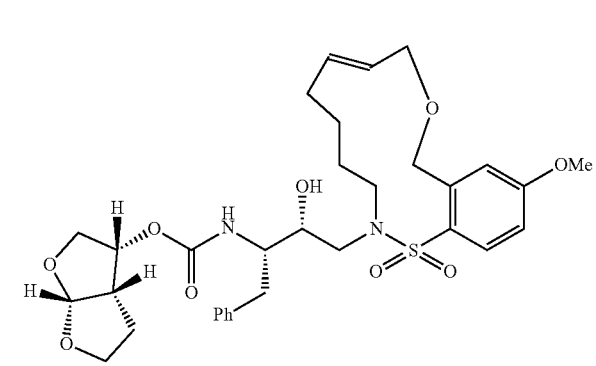
2
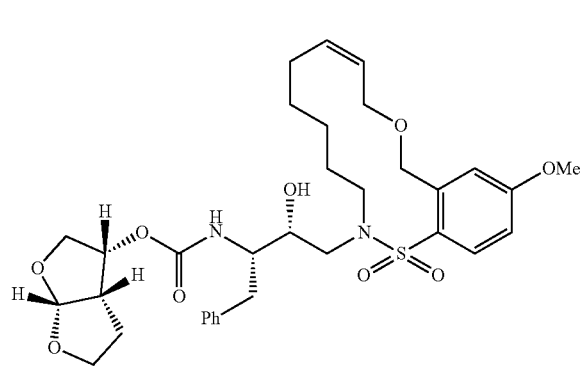
3
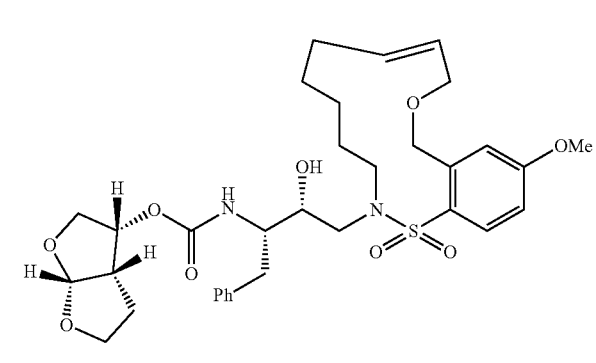
4
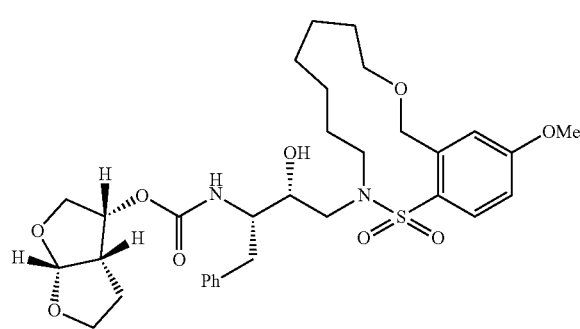
5
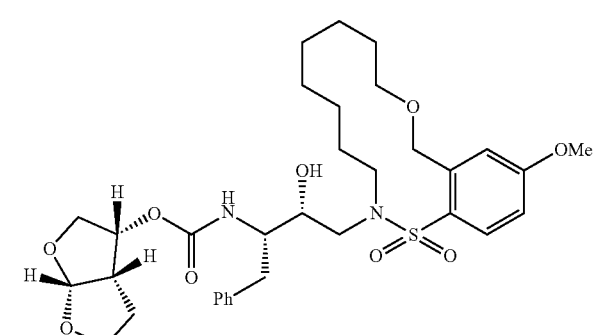
6
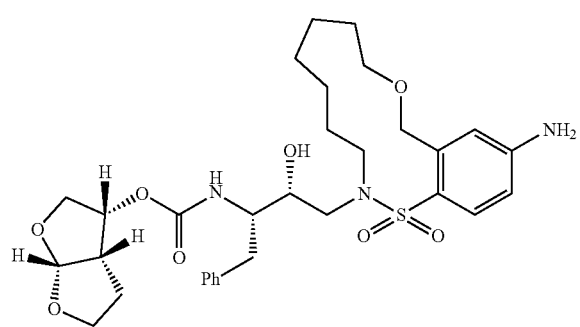
7
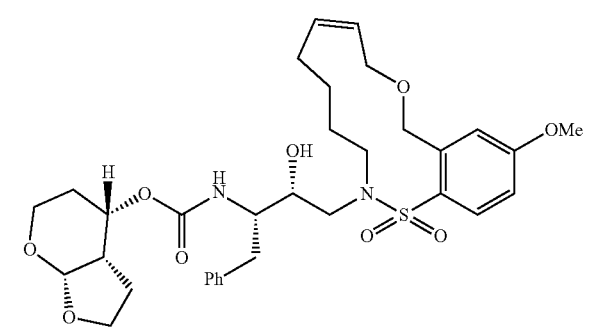
8

-continued
9
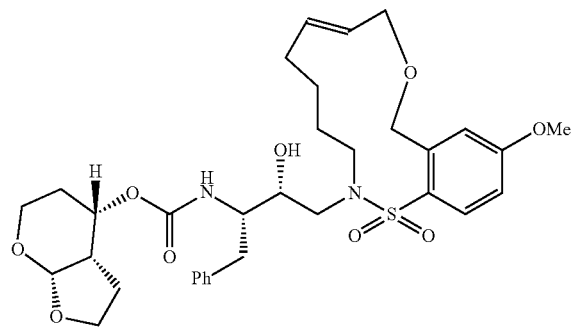
10
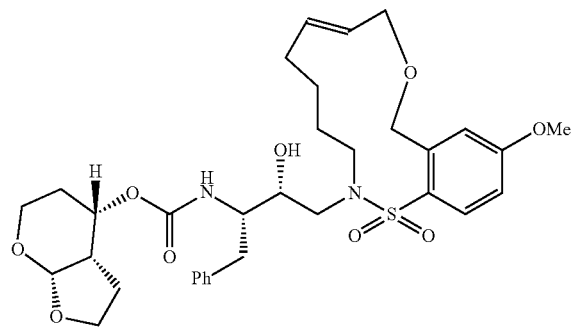
11
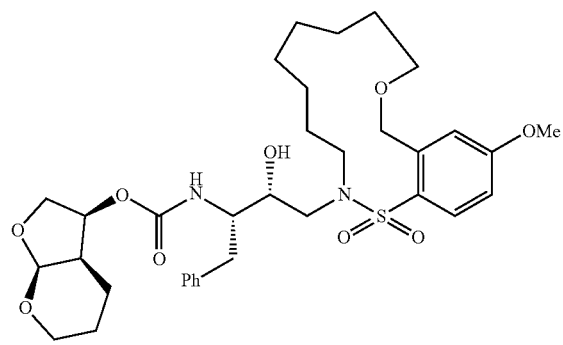
12
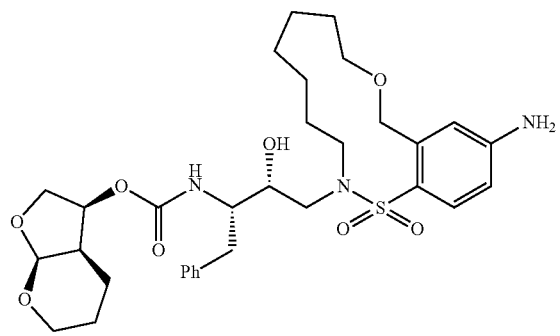
13
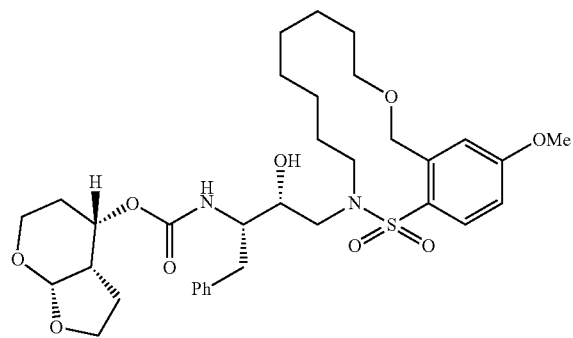
14
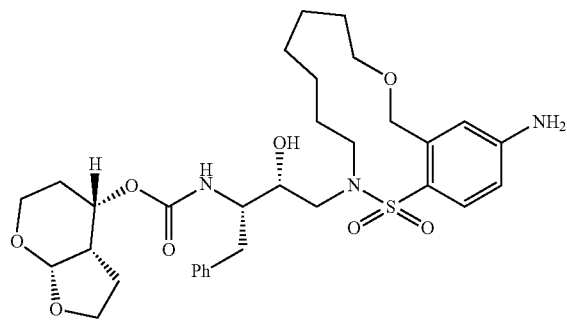
15
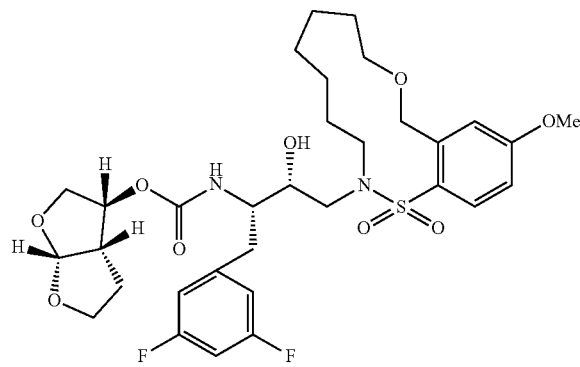
16
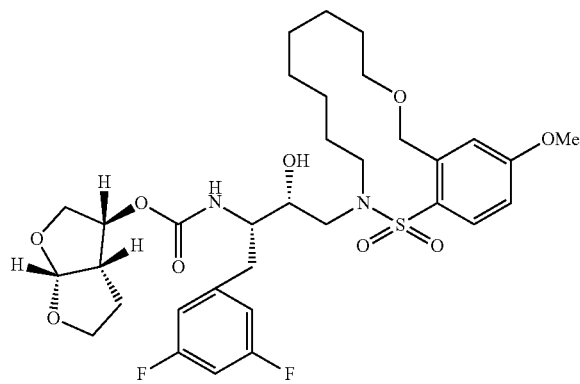

-continued
| 17 | 18 |
|---|---|
| 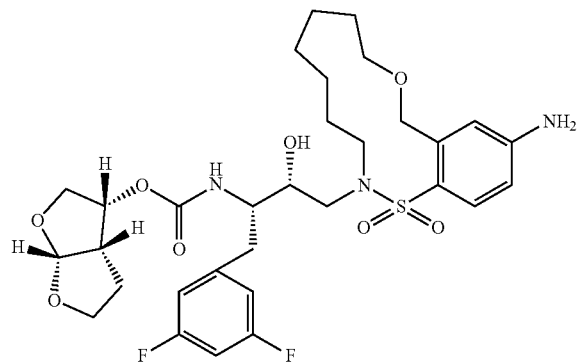 | 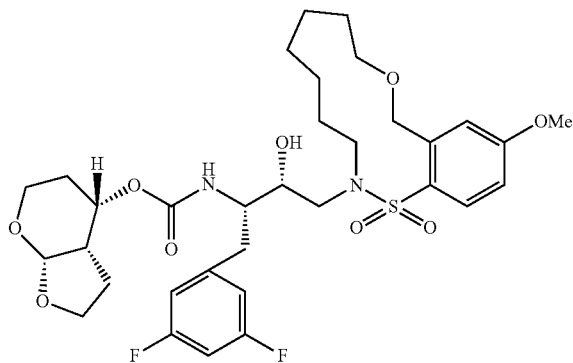 |
| 19 | 20 |
|---|---|
| 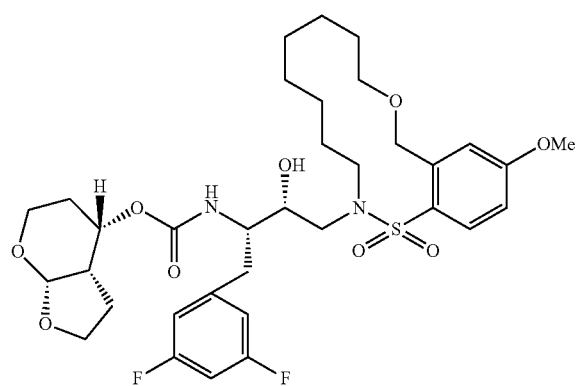 | 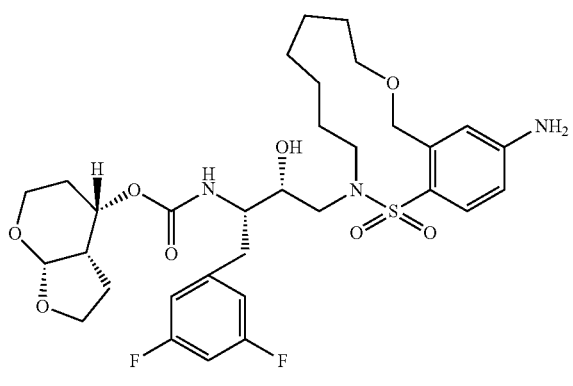 |
| 21 | 22 |
|---|---|
| 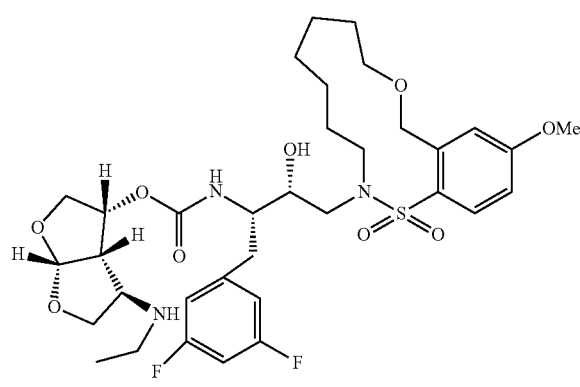 | 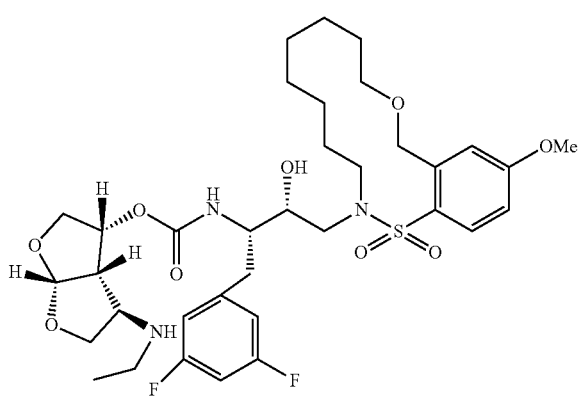 |
| 23 | 24 |
|---|---|
| 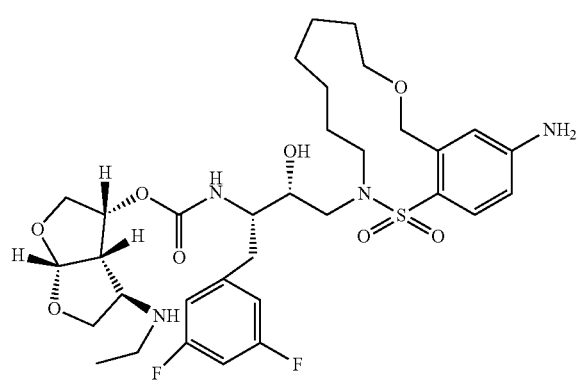 | 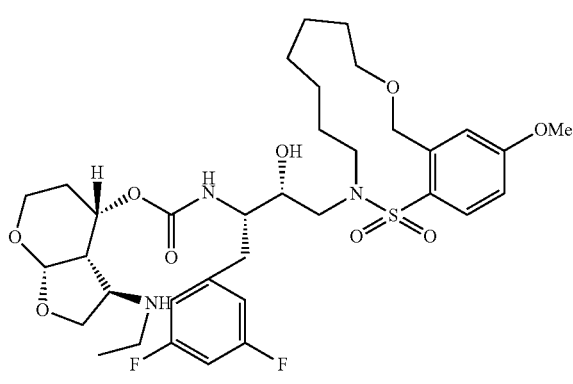 |

-continued
| 25 | 26 |
|---|---|
| 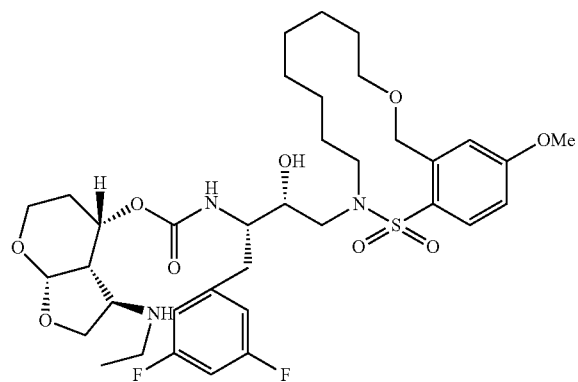 | 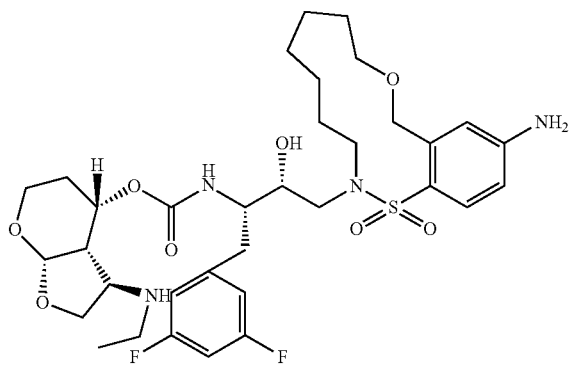 |
| 27 | 28 |
| 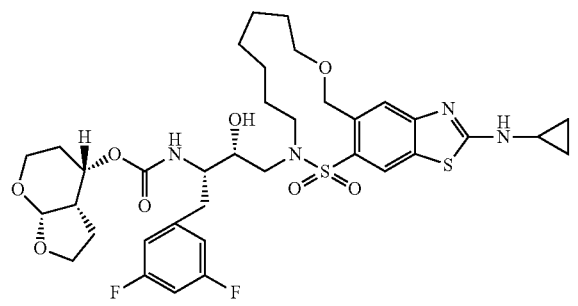 | 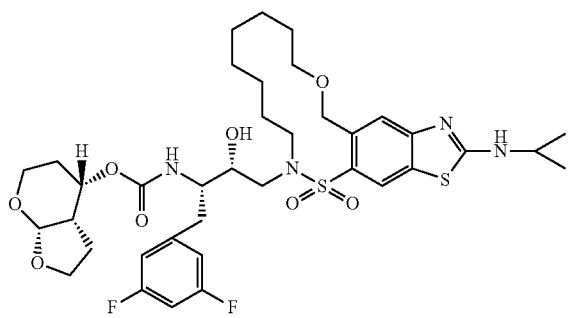 |
| 29 | 30 |
| 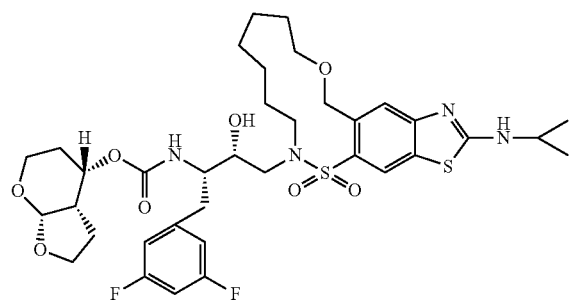 | 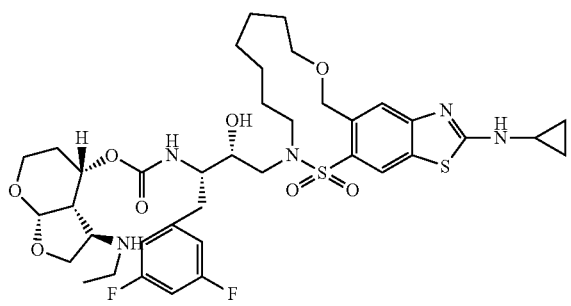 |
| 31 | 32 |
| 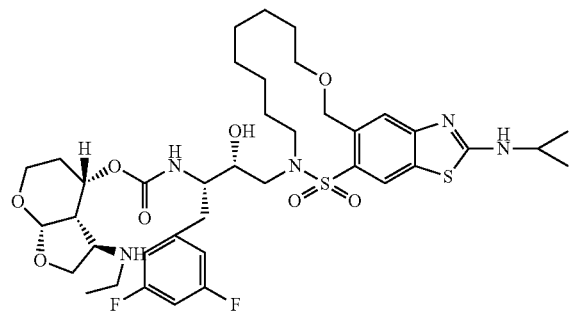 | 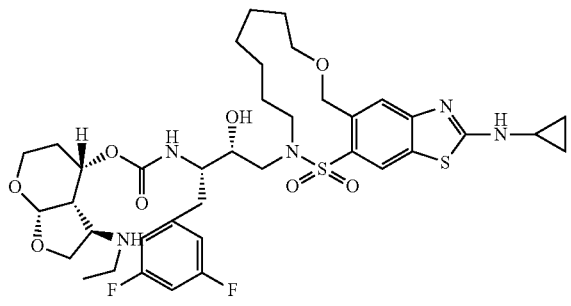 |

-continued
33
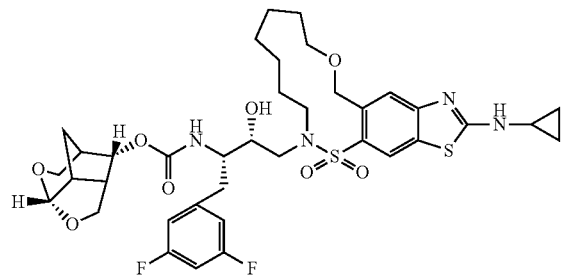
34
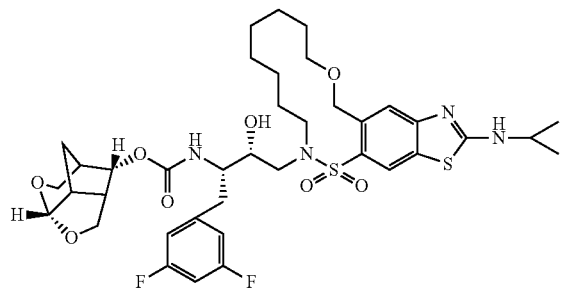
35
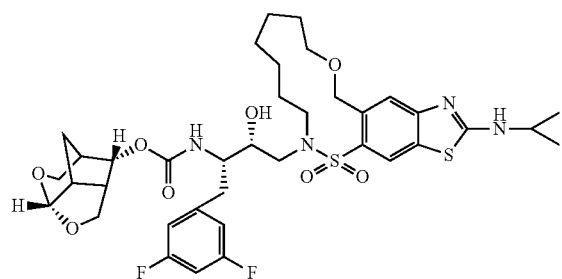
36
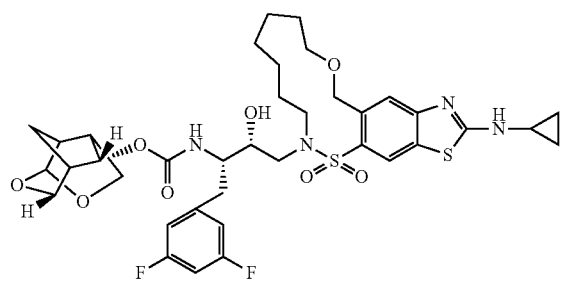
37
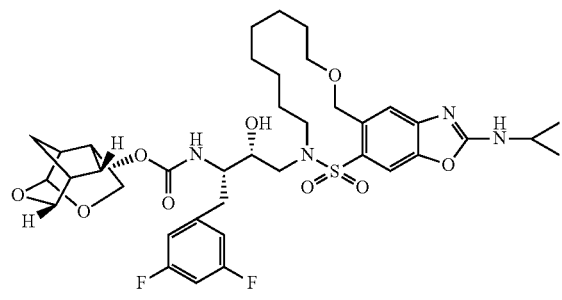
38
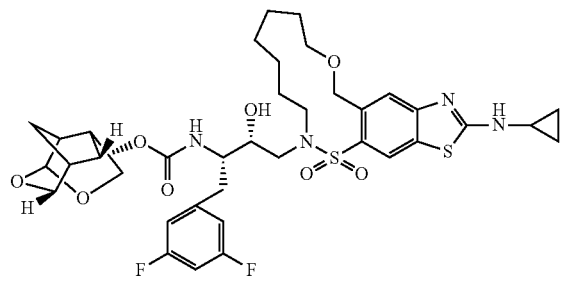
54
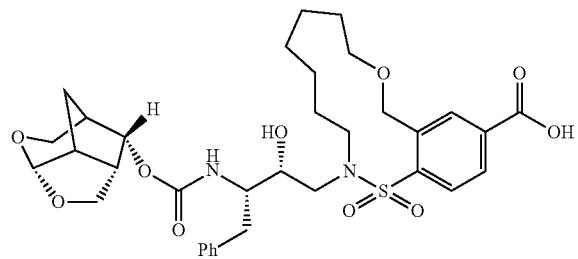
55
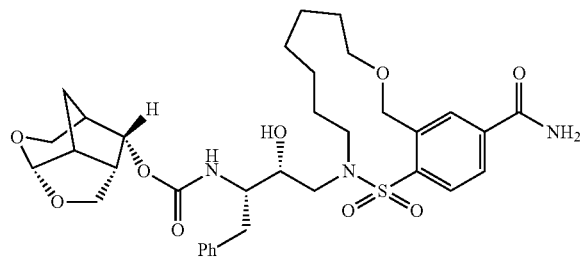
56
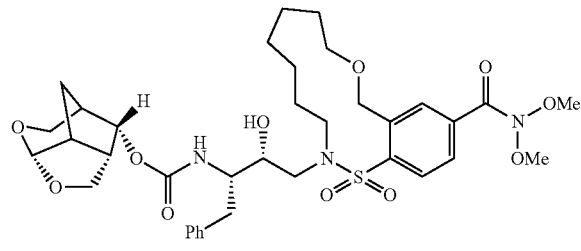
57
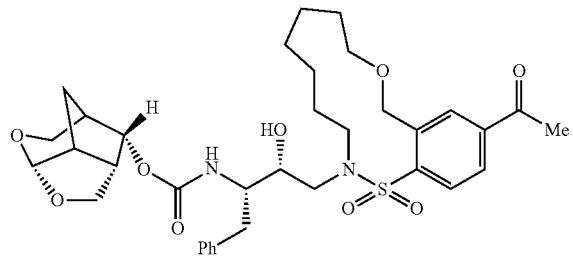

58
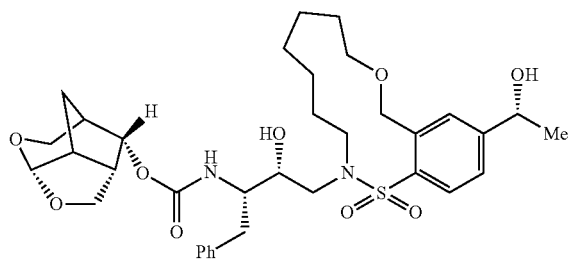
59
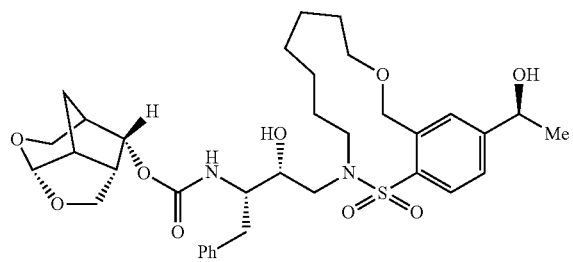
60
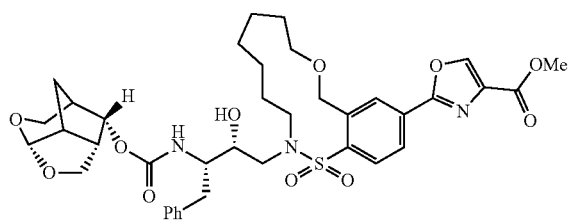
61
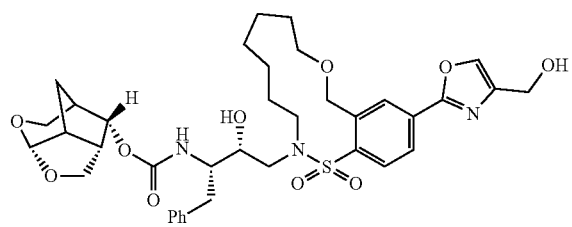
62
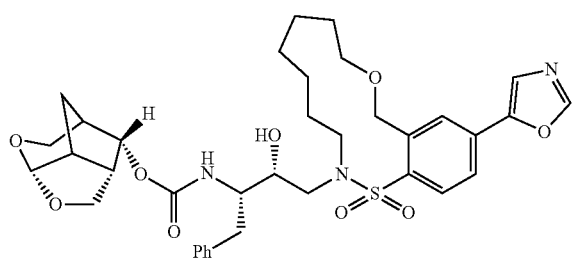
63
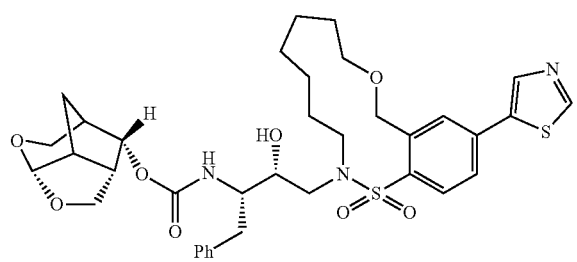
64
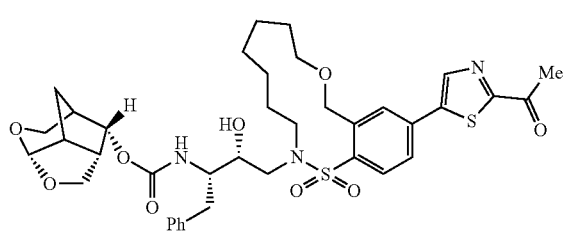
65
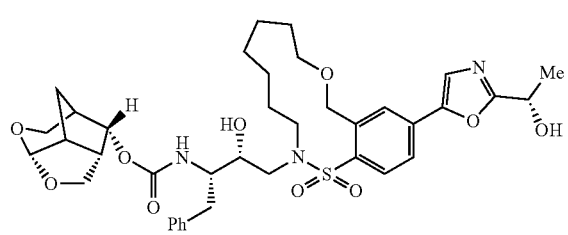
66
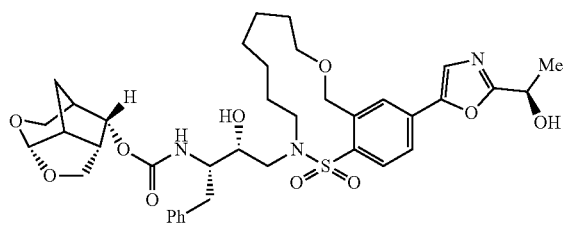
67
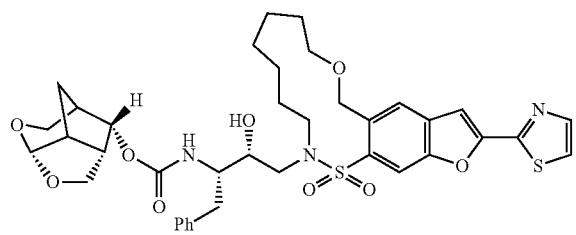
68
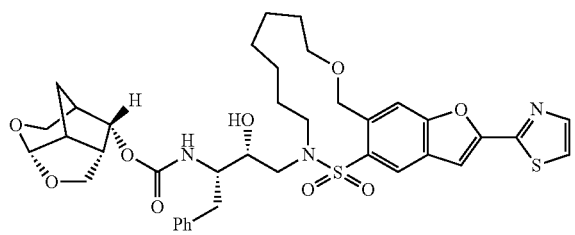
69
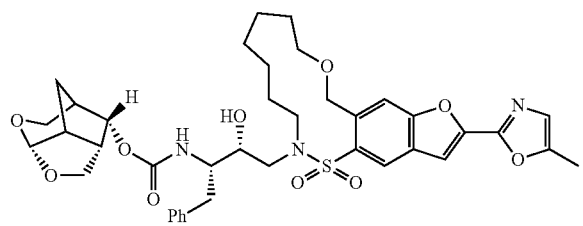

or a pharmaceutically acceptable salt, crystalline form, non-crystalline form, hydrate, or solvate thereof.

6. A pharmaceutical composition comprising one or more compounds of claim 1 and one or more pharmaceutically acceptable carriers, diluents, excipients or combinations thereof.

7. A method for treating a patient in need of relief from HIV/AIDS, the method comprising the step of administering to the patient a therapeutically effective amount of a compound of claim 1.

8. A pharmaceutical composition comprising one or more compounds of claim 4 and one or more pharmaceutically acceptable carriers, diluents, excipients or combinations thereof.

9. A method for treating a patient in need of relief from HIV/AIDS, the method comprising the step of administering to the patient a therapeutically effective amount of a compound of claim 4.

10. A pharmaceutical composition comprising one or more compounds of claim 5 and one or more pharmaceutically acceptable carriers, diluents, excipients or combinations thereof.

11. A method for treating a patient in need of relief from HIV/AIDS, the method comprising the step of administering to the patient a therapeutically effective amount of a compound of claim 5.

12. A compound of the formula (I):

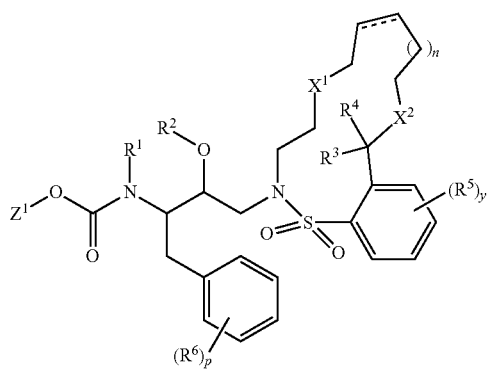

or a pharmaceutically acceptable salt, stereoisomer, crystalline form, non-crystalline form, hydrate, or solvate thereof wherein:

the dashed line represents an E- or Z-double bond;

$Z^1$ is:

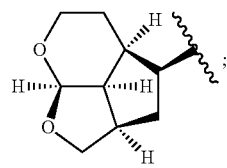

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, S, S(O), $SO_2$, optionally substituted nitrogen, or optionally substituted alkylene;

each $R^5$ is independently hydrogen, $—OR^b$, wherein $R^b$ is alkyl or aryl, $—SO_2R^7$, $R_2^7$, $—CHR^7OR^7$ or $CR_3^7$, wherein each $R^7$ is independently hydrogen, alkyl, heteroalkyl or heterocyclyl or two adjacent $R^5$ groups, together with the carbon atoms to which they are attached, form a heteroaryl group;

each $R^6$ is independently hydrogen, halo, $—NR_2^7$, alkyl, aryl, alkylaryl, heteroalkyl or heterocyclyl;

y is an integer from 1 to 3;

p is an integer from 1 to 3; and n is an integer from 0 to 4.

13. The compound of claim 12, wherein the compound of the formula (I) is a compound of the formula (Ia):

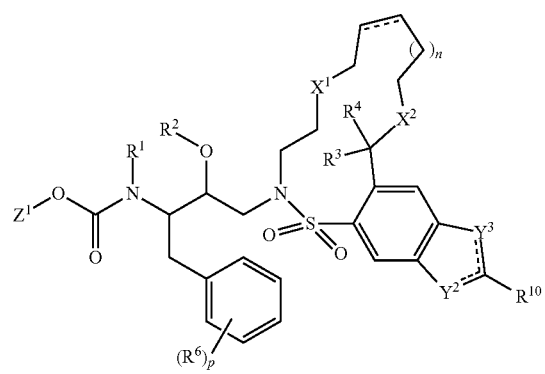

or a pharmaceutically acceptable salt, stereoisomed, crystalline form, non-crystalline form, hydrate, or solvate thereof wherein:

the dashed line represents an E- or Z-double bond;

$Z^1$ is:

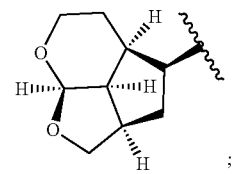

$R^1$ and $R^2$ are each independently hydrogen, alkyl or arylalkyl;

$R^3$ and $R^4$ are each independently H, alkyl or $R^3$ and $R^4$, together with the carbon atom to which they are attached, form a cycloalkyl or a heterocyclyl group;

$X^1$ and $X^2$ are each independently oxygen, S, S(O), $SO_2$, optionally substituted nitrogen, or optionally substituted alkylene;

each $R^6$ is independently hydrogen, halo, $—NR_2^7$, alkyl, aryl, alkylaryl, heteroalkyl or heterocyclyl;

$R^{10}$ is $—OR^9$ or $—NR_2^9$, wherein each $R^9$ is independently hydrogen, alkyl, cycloalkyl, heteroalkyl or heterocyclyl;

$Y^2$ and $Y^3$ are each independently N, S, O, $NR^9$ or $CR^{11}$, wherein each $R^{11}$ is independently hydrogen, alkyl, aryl, or heteroeyelyl;

p is an integer from 1 to 3; and n is an integer from 0 to 4.

14. A compound of the formula:
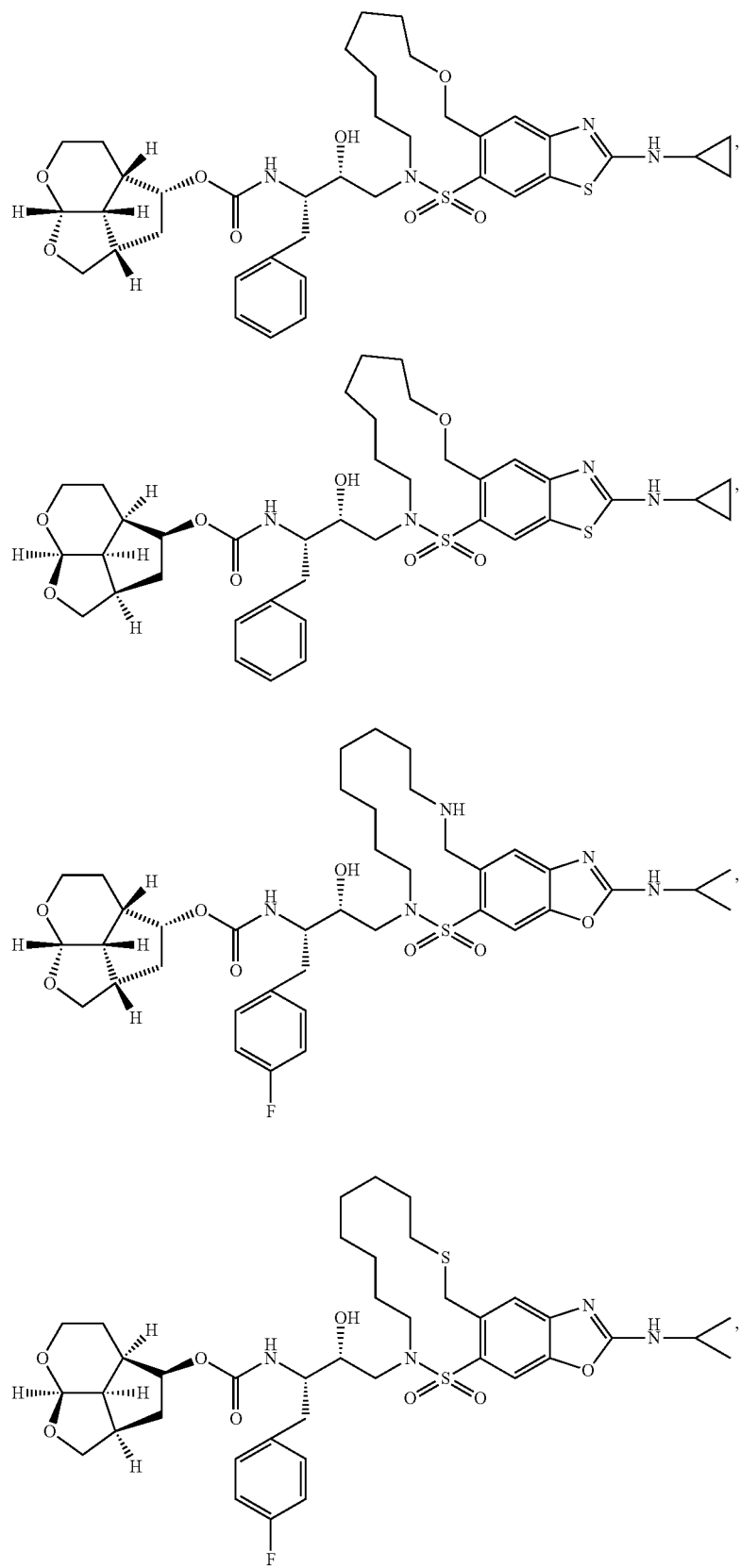

-continued
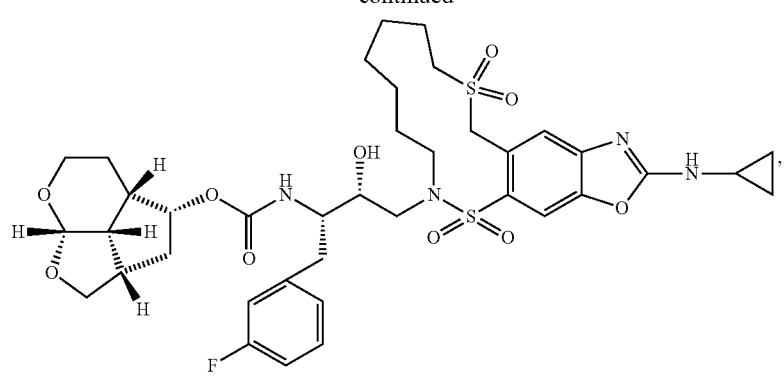
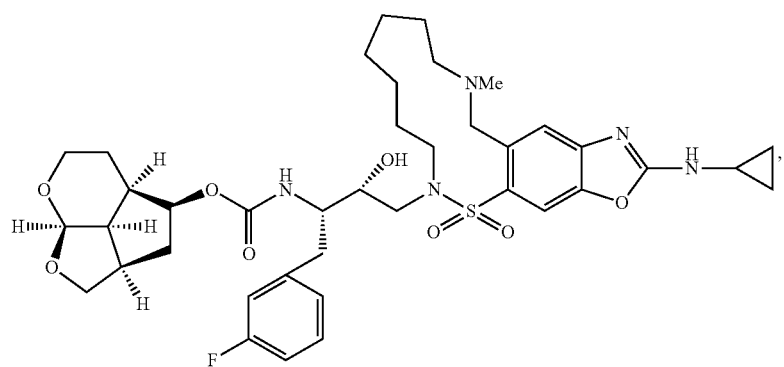
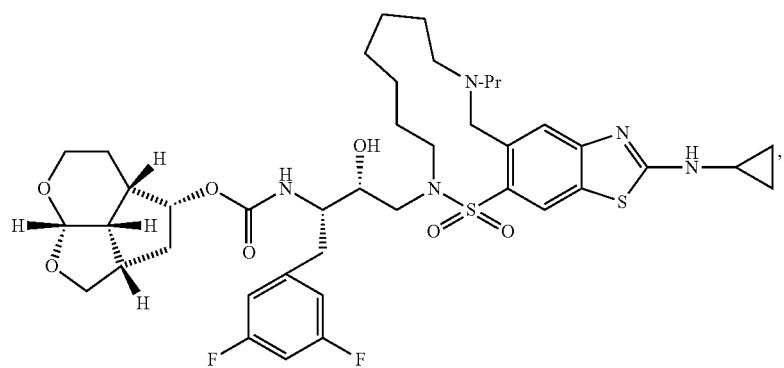
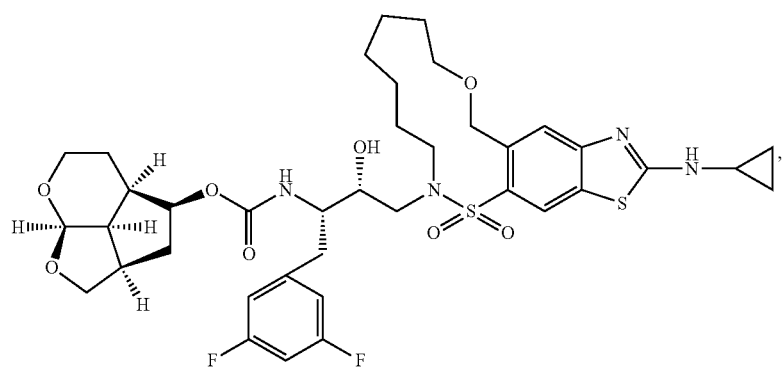

-continued
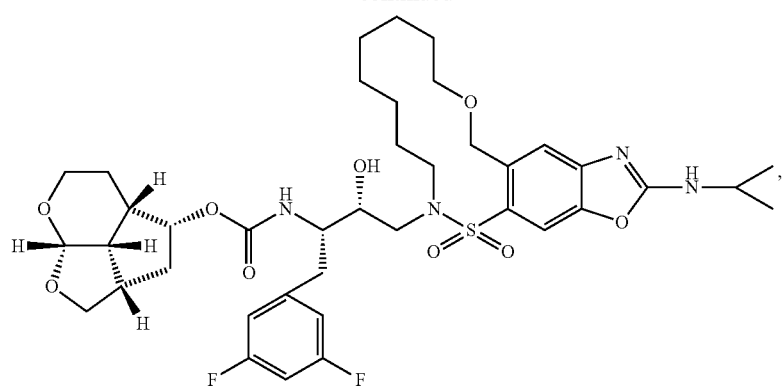
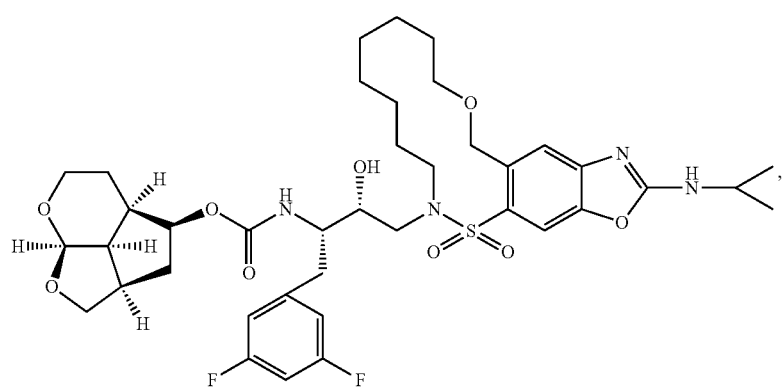
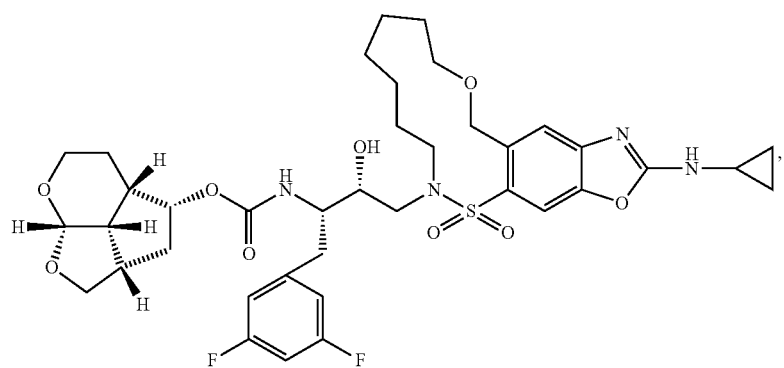
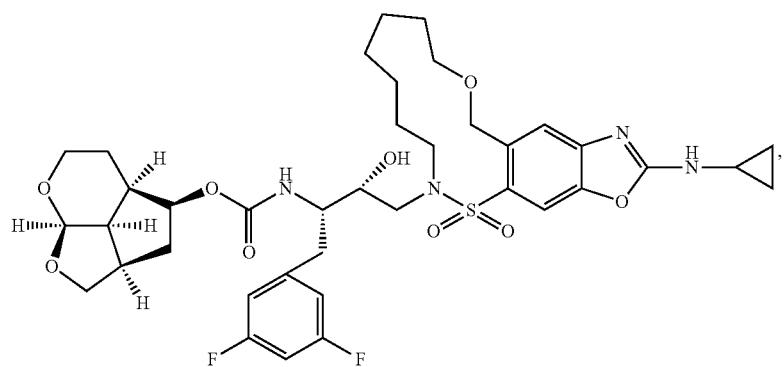

or a pharmaceutically acceptable salt, crystalline form, non-crystalline form, hydrate, or solvate thereof.

15. A pharmaceutical composition comprising one or more compounds of claim 12 and one or more pharmaceutically acceptable carriers, diluents, excipients or combinations thereof.

16. A method for treating a patient in need of relief from HIV/AIDS, the method comprising the step of administering to the patient a therapeutically effective amount of a compound of claim 12.

17. A pharmaceutical composition comprising one or more compounds of claim 13 and one or more pharmaceutically acceptable carriers, diluents, excipients or combinations thereof.

18. A method for treating a patient in need of relief from HIV/AIDS, the method comprising the step of administering to the patient a therapeutically effective amount of a compound of claim 13.

19. A pharmaceutical composition comprising one or more compounds of claim 14 and one or more pharmaceutically acceptable carriers, diluents, excipients or combinations thereof.

20. A method for treating a patient in need of relief from HIV/AIDS, the method comprising the step of administering to the patient a therapeutically effective amount of a compound of claim 14.

\* \* \* \* \*